United States Patent
Knopfmacher et al.

(10) Patent No.: US 9,963,733 B2
(45) Date of Patent: May 8, 2018

(54) DEVICES, SYSTEMS AND METHODS FOR DETECTING VIABLE INFECTIOUS AGENTS IN A FLUID SAMPLE

(71) Applicant: eSense, LLC, Menlo Park, CA (US)

(72) Inventors: Oren S. Knopfmacher, Palo Alto, CA (US); Meike Herget, Woodside, CA (US); Michael D. Laufer, Menlo Park, CA (US); August Estabrook, South San Francisco, CA (US)

(73) Assignee: Avails Medical, Inc., Menlo Park, CA (US)

( * ) Notice: Subject to any disclaimer, the term of this patent is extended or adjusted under 35 U.S.C. 154(b) by 26 days.

(21) Appl. No.: 14/878,936

(22) Filed: Oct. 8, 2015

(65) Prior Publication Data
US 2017/0059508 A1   Mar. 2, 2017

Related U.S. Application Data

(60) Provisional application No. 62/209,754, filed on Aug. 25, 2015.

(51) Int. Cl.
*G01N 27/327*   (2006.01)
*C12Q 1/02*   (2006.01)
(Continued)

(52) U.S. Cl.
CPC ............... *C12Q 1/18* (2013.01); *C12Q 1/025* (2013.01); *G01N 27/3275* (2013.01);
(Continued)

(58) Field of Classification Search
CPC ............... C12M 23/16; G01N 27/4145; G01N 27/4148; G01N 33/5011; C12Q 1/18
See application file for complete search history.

(56) References Cited

U.S. PATENT DOCUMENTS 4,448,534 A * 5/1984 Wertz ...................... C12M 41/36
356/435
5,064,756 A * 11/1991 Carr ......................... C12Q 1/04
435/18
(Continued)

FOREIGN PATENT DOCUMENTS

WO   WO 2007/035814   3/2007
WO   WO 2010/062001   6/2010
(Continued)

*Primary Examiner* — Krishnan S Menon
*Assistant Examiner* — Dwan A Gerido
(74) *Attorney, Agent, or Firm* — Levine Bagade Han LLP

(57) ABSTRACT

Various devices, systems and methods for detecting a susceptibility of an infectious agent to an anti-infective are described herein. A method comprises introducing a fluid sample to a first surface and a second surface; exposing the first surface to a first solution; exposing the second surface to a second solution, wherein the second surface comprises an anti-infective; sampling the first solution after exposing the first solution to the first surface; sampling the second solution after exposing the second solution to the second surface; monitoring a first electrical characteristic of a first sensor exposed to the first solution sampled; monitoring a second electrical characteristic of a second sensor exposed to the second solution sampled; and comparing the first electrical characteristic and the second electrical characteristic to assess the susceptibility of the infectious agent to the anti-infective.

16 Claims, 18 Drawing Sheets

(51) Int. Cl.
*C12Q 1/18* (2006.01)
*G01N 33/50* (2006.01)
*G01N 27/414* (2006.01)
*C12M 3/06* (2006.01)

(52) U.S. Cl.
CPC ..... *G01N 27/4145* (2013.01); *G01N 33/5011* (2013.01); *C12M 23/16* (2013.01); *G01N 27/4148* (2013.01)

(56) References Cited

U.S. PATENT DOCUMENTS

| | | |
|---|---|---|
| 2007/0072187 A1 | 3/2007 | Blok et al. |
| 2011/0306032 A1* | 12/2011 | Galiano ............... G01N 35/028 435/3 |
| 2012/0261274 A1* | 10/2012 | Rearick ................. G01N 27/27 205/789 |
| 2014/0231256 A1* | 8/2014 | Packingham ........ G01N 1/4077 204/572 |
| 2015/0355129 A1 | 12/2015 | Knopfmacher |
| 2016/0187332 A1 | 6/2016 | Herget et al. |
| 2017/0058313 A1 | 3/2017 | Knopfmacher et al. |

FOREIGN PATENT DOCUMENTS

| | | | |
|---|---|---|---|
| WO | 2013/096404 | * | 6/2013 |
| WO | WO 2014/134431 | | 9/2014 |
| WO | WO 2017/035393 | | 3/2017 |

\* cited by examiner

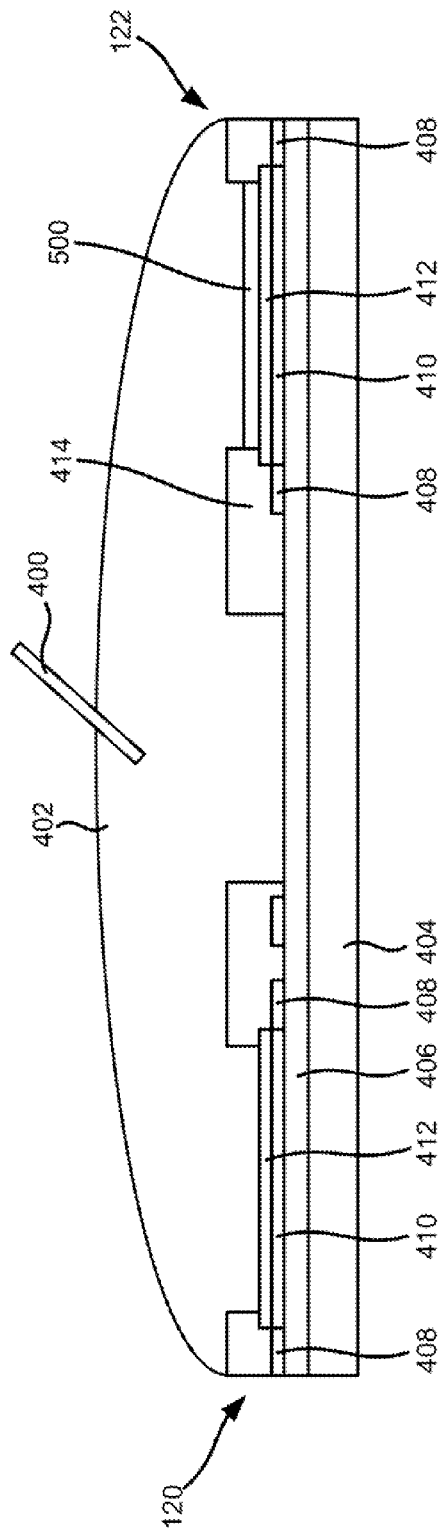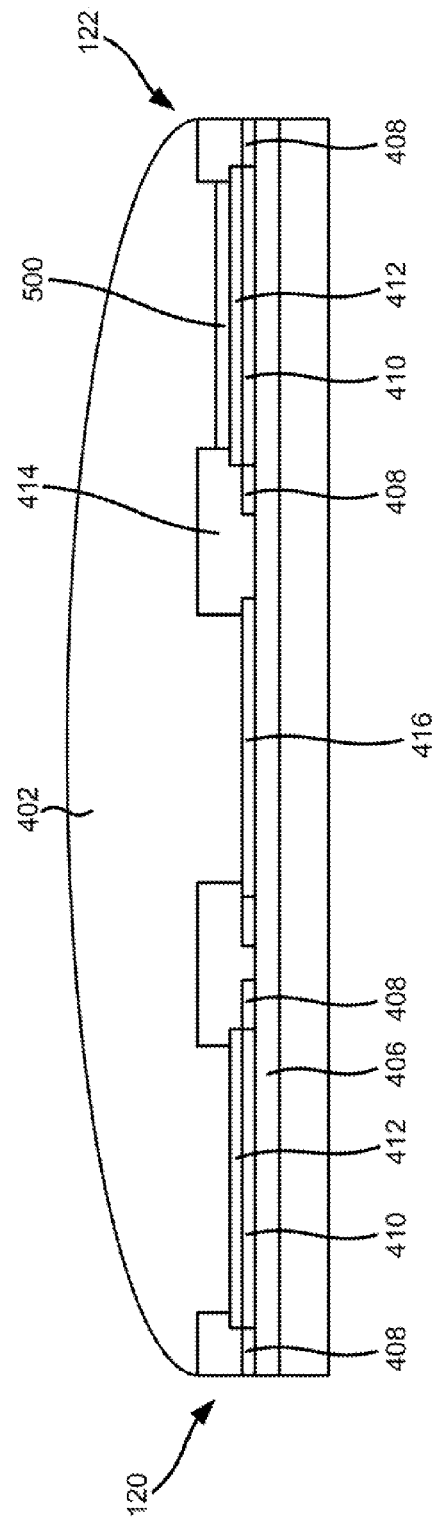
FIGURE 5A
FIGURE 5B

DEVICES, SYSTEMS AND METHODS FOR DETECTING VIABLE INFECTIOUS AGENTS IN A FLUID SAMPLE

CROSS-REFERENCE TO RELATED APPLICATIONS

This application claims the benefit of U.S. Provisional Patent Application No. 62/209,754 filed on Aug. 25, 2015, the content of which is incorporated herein by reference in its entirety. This application also incorporates by reference the content of U.S. patent application Ser. No. 14/297,603 filed on Jun. 5, 2014 and U.S. patent application Ser. No. 14/599,190 filed on Jan. 16, 2015 in their entireties.

FIELD OF THE INVENTION

The present disclosure relates generally to in vitro detection of infectious agents and, more specifically, to devices, systems, and methods for detecting viable infectious agents in a fluid sample.

BACKGROUND

Infections caused by anti-infective resistant infectious agents or microbes are a significant problem for healthcare professionals in hospitals, nursing homes, and other healthcare environments. For example, such infections can lead to a potentially life-threatening complication known as sepsis where chemicals released into the bloodstream by an infectious agent can trigger a dangerous whole-body inflammatory response as well as a vasoactive response causing fever, low blood pressure, and possibly death. When faced with such an infection, a preferred course of action is for a clinician to use anti-infective compounds judiciously, preferably only those necessary to alleviate the infection. However, what occurs most frequently today is that until the organism is identified and tested for drug sensitivity, broad spectrum anti-infectives, often multiple drugs, are given to the patient to insure adequacy of treatment. This tends to result in multiple drug resistant infectious agents. Ideally, the sensitivity of the infectious agent would be detected soon after its presence is identified. The present disclosure presents devices, systems, and methods for accomplishing this goal.

Existing methods and instruments used to detect anti-infective resistance in infectious agents include costly and labor intensive microbial culturing techniques to isolate the infectious agent and include tests such as agar disk diffusion or broth microdilution where anti-infectives are introduced as liquid suspensions, paper disks, or dried gradients on agar media. However, those methods require manual interpretation by skilled personnel and are prone to technical or clinician error.

While automated inspection of such panels or media can reduce the likelihood of clinician error, current instruments used to conduct these inspections are often costly and require constant maintenance. In addition, current instruments often rely on an optical read-out of the investigated samples requiring bulky detection equipment and access to power supplies. Most importantly, these methods require days to obtain a result, as the infectious agents must reproduce several times in different media prior to being exposed to the anti-infective to determine their susceptibility.

In addition, such methods and instruments often cannot conduct such tests directly on a patient's bodily fluids and require lengthy sample preparation times.

As a result of the above limitations and restrictions, there is a need for improved devices, systems, and methods to quickly and effectively detect anti-infective resistant infectious agents in a patient sample.

SUMMARY

Various devices, systems and methods for detecting the susceptibility of an infectious agent in a patient sample to one or more anti-infectives are described herein.

In one embodiment, a method for detecting the susceptibility of an infectious agent to one or more anti-infectives can include introducing a fluid sample to a first surface and a second surface, exposing the first surface to a first solution, and exposing the second surface to a second solution. The second surface can comprise an anti-infective.

In some instances, the fluid sample can comprise the infectious agent and the infectious agent can be introduced to the first surface or the second surface through the fluid sample. The method can also include determining the presence of the infectious agent in the fluid sample.

The method can include sampling the first solution after exposing the first solution to the first surface. The method can also include sampling the second solution after exposing the second solution to the second surface. The method can include monitoring a first electrical characteristic of a first sensor exposed to the first solution sampled. The method can include monitoring a second electrical characteristic of a second sensor exposed to the second solution sampled.

The method can further include comparing the first electrical characteristic and the second electrical characteristic to assess the susceptibility of the infectious agent to the anti-infective. Comparing the first electrical characteristic and the second electrical characteristic can include determining a difference between the first electrical characteristic and the second electrical characteristic. The difference between the first electrical characteristic and the second electrical characteristic can be a result of a difference in a solution characteristic of the first solution and the second solution. The difference in the solution characteristic of the first solution and the second solution can result from a difference in a molecular count, a concentration of an ion, and/or a solution temperature.

The first surface can be a filter surface or a well surface. The second surface can be separate from the first surface and can be another instance of the filter surface or the well surface. At least one of the first surface and the second surface can be a non-clogging filter. In addition, at least one of the first surface and the second surface can comprise pores of sequentially smaller pore size.

The infectious agent can be, but is not limited to, a bacteria, a fungus, a virus, or a prion. The first sensor and the second sensor can be housed by a protective chamber and the protective chamber can be an electrically isolated environment, a temperature controlled chamber, and/or a light controlled chamber. The first solution can be directed to the first surface by a pump. The second solution can also be directed to the second surface by a pump.

In another embodiment, a method for detecting a susceptibility of an infectious agent to an anti-infective can include introducing a fluid sample to a first surface and a second surface, exposing the first surface to a first solution, and exposing the second surface to a second solution. The second surface can comprise an anti-infective.

In some instances, the fluid sample can comprise the infectious agent and the infectious agent can be introduced to the first surface or the second surface through the fluid sample. The method can also include determining the presence of the infectious agent in the fluid sample.

The method can include sampling the first solution after exposing the first solution to the first surface. The method can also include sampling the second solution after exposing the second solution to the second surface. The method can include monitoring a first electrical characteristic of a sensor exposed to the first solution sampled. The method can also include monitoring a second electrical characteristic of the sensor exposed to the second solution sampled.

The method can further include comparing the first electrical characteristic and the second electrical characteristic to assess the susceptibility of the infectious agent to the anti-infective. Comparing the first electrical characteristic and the second electrical characteristic can include determining a difference between the first electrical characteristic and the second electrical characteristic. The difference between the first electrical characteristic and the second electrical characteristic can be a result of a difference in a solution characteristic of the first solution and the second solution. The difference in the solution characteristic of the first solution and the second solution can result from a difference in a molecular count, a concentration of an ion, and/or a solution temperature.

The first surface can be a filter surface or a well surface. The second surface can be separate from the first surface and can be another instance of the filter surface or the well surface. At least one of the first surface and the second surface can be a non-clogging filter. In addition, at least one of the first surface and the second surface can comprise pores of sequentially smaller pore size.

The infectious agent can be, but is not limited to, a bacteria, a fungus, a virus, or a prion. The first sensor and the second sensor can be housed by a protective chamber and the protective chamber can be an electrically isolated environment, a temperature controlled chamber, and/or a light controlled chamber. The first solution can be directed to the first surface by a pump. The second solution can also be directed to the second surface by a pump.

BRIEF DESCRIPTION OF THE SEVERAL VIEWS OF THE DRAWINGS

FIG. 5A illustrates a side view of an embodiment of a substrate having the active sensor and a control sensor disposed on the substrate and an external reference electrode.

FIG. 5B illustrates a side view of an embodiment of a substrate having the active sensor, the control sensor, and the on-chip reference electrode disposed on the substrate.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
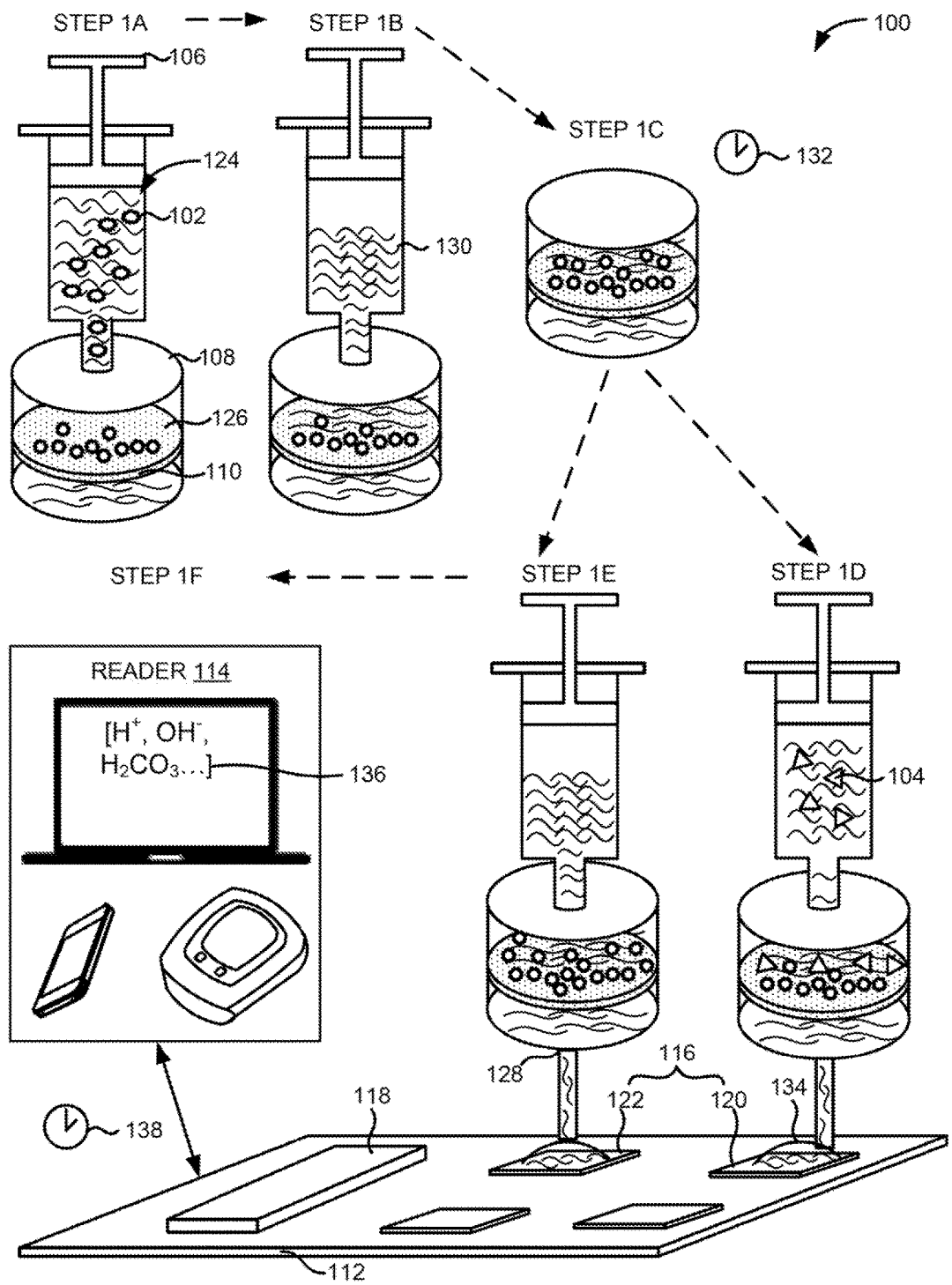
FIG. 1 illustrates one embodiment of a system for detecting a susceptibility of an infectious agent to one or more anti-infectives.

FIG. 1 illustrates an embodiment of a system 100 for detecting or assessing a susceptibility of an infectious agent 102 to an anti-infective 104. The system 100 can comprise a fluid delivery device 106, a filter housing 108 containing a filter 110, a substrate 112, and a reader 114. The substrate 112 can have one or more sensors 116 disposed on a surface of the substrate 112. The substrate 112 can be comprised of a polymeric material, a metal, a ceramic, a semiconductor layer, an oxide layer, an insulator, or a combination thereof. The system 100 can also include an analyzer 118. In the embodiment shown in FIG. 1, the analyzer 118 can be disposed on a surface of the substrate 112. In other embodiments, the analyzer 118 can be a standalone unit or device coupled to the substrate 112.

The sensors 116 can include one or more active sensors 120, one or more control sensors 122, or a combination thereof. As illustrated in the embodiment shown in FIG. 1, the one or more active sensors 120 and control sensors 122 can be disposed on the same side surface of the substrate 112. In other embodiments not shown in FIG. 1, the active sensors 120 and the control sensors 122 can be disposed on different surfaces of the substrate 112, different substrates 112, or a combination thereof. For example, FIG. 1 shows the substrate 112 having four sensors 116; however, it is contemplated that the substrate 112 can comprise any number of sensors 116. In one embodiment, at least one of the sensors 116 can be an ion-sensitive field effect transistor (ISFET). The sensors 116 will be discussed in more detail in the sections that follow.

The system 100 can detect or assess the level of susceptibility of the infectious agent 102 to an anti-infective 104. In some instances, the fluid sample 124 can comprise the infectious agent 102. The fluid sample 124 can include a bodily fluid such as blood, serum, plasma, urine, saliva, joint fluid, semen, wound material, spinal fluid, mucus, or a combination thereof. In other embodiments, the fluid sample 124 can also include an environmental fluid such as liquids sampled from a stream, river, lake, ocean, contamination site, quarantine zone, or emergency area. The fluid sample 124 can also be a food sample. The system 100 can determine the presence of the infectious agent 102 in the fluid sample 124 before detecting or assessing the level of susceptibility of the infectious agent 102 to the anti-infective 104.

The infectious agent 102 can be any metabolizing single or multi-cellular organism including a bacteria or fungus. The infectious agent 102 can also be a virus or a prion.

In certain embodiments, the infectious agent 102 can be a bacteria selected from the genera consisting of *Acinetobacter, Aeromonas, Bacillus, Bacteroides, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella, Stenotrophomonas, Streptomyces, Staphylococcus, Enterococcus, Clostridium* or any combination thereof. In other embodiments, the infectious agent 102 can be a fungus selected from the genera consisting of *Candida, Cryptococcus*, or any combination thereof. In another embodiment, the infectious agent 102 can include amoeba. In further embodiments, the infectious agent 102 can be cancer cells and the anti-infectives 104 can be chemotherapeutics or other cancer treatments.

As illustrated in FIG. 1, the fluid delivery device 106 can deliver or inject the fluid sample 124 into the filter housing 108 in step 1A. The fluid sample 124 injected can comprise the infectious agent 102. In the example embodiment shown in FIG. 1, the fluid delivery device 106 can be a pump. For example, the fluid delivery device 106 can be a syringe pump, a pneumatic pump, or a hydraulic pump. In other embodiments not shown in FIG. 1, the fluid delivery device 106 can be an injection cartridge, a microfluidic channel, a pipette, a reaction tube, a capillary, a test tube, a combination thereof, or a portion therein.

The filter housing 108 can be a container or vessel configured to secure or enclose the filter 110. The filter housing 108 can also be a protective chamber. The protective chamber can be an electrically isolated environment, a temperature controlled chamber, and/or a light controlled chamber. For example, the filter housing 108 can be a housing of a syringe filter.

The filter 110 can be a non-clogging filter. The filter 110 can have a non-clogging filter surface. The filter 110 can also have filter pores of sequentially smaller pore size. For example, the filter 110 can have larger filter pores at the top of the filter and progressively smaller filters pores toward the bottom of the filter 110. Although not shown in FIG. 1, it is contemplated by this disclosure that the filter 110 can refer to a plurality of filters in a stacked arrangement.

The filter 110 can be a mesh or matrix for isolating or separating the infectious agent 102 or other molecules or cells from the supernatant of the fluid sample 124. In certain embodiments, the filter 110 can be selected from the group consisting of cellulose acetate, regenerated cellulose, nylon, polystyrene, polyvinylidene fluoride (PVDF), polyethersulfone (PES), polytetrafluorethylene (PTFE), glass fiber polypropylene, or a combination thereof.

The filter 110 can comprise a filter surface 126. The filter surface 126 can be the portion of the filter 110 used to isolate or trap the infectious agent 102. The filter surface 126 can include an external surface, an internal surface extending into the filter 110, or a combination thereof. The filter housing 108 can have at least one opening 128 which allow fluid or supernatant from the fluid sample 124 to evacuate the filter housing 108. For example, step 1A can include the additional step of discarding the fluid or supernatant from the fluid sample 124 through the opening 128 after isolating the infectious agent 102 on the filter surface 126.

In another embodiment not shown in FIG. 1, a stimulus solution can be added to the fluid sample 124 before introducing the fluid sample 124 to the filter 110. The stimulus solution can be a nutrient or growth solution. The stimulus solution can have a different composition than the nutrient solution 130. The stimulus solution can be a super nutrient solution.

In an alternative embodiment not shown in FIG. 1, the fluid sample 124 can be pre-filtered in a step before step 1A. This pre-filtering step can involve filtering the fluid sample 124 using another instance of the filter 110, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject a nutrient solution 130 to the filter housing 108 in step 1B. The fluid delivery device 106 can continuously or periodically expose the filter surface 126 containing the infectious agent 102 with the nutrient solution 130. In one embodiment, the nutrient solution 130 can be composed of a buffer containing bacto-tryptone, yeast extract, sodium chloride and any combinations thereof. In another embodiment the nutrient solution can include a growth inducer. The growth inducer can be selected from the group consisting of a carbon-based inducer, a nitrogen-based inducer, a mineral, a trace element, a biological growth factor, or any combination thereof. For example, the growth inducer can include but is not limited to glucose, ammonia, magnesium, or a combination thereof. For example, the nutrient solution 130 can be comprised of Tryptone, yeast extract, NaCl, and glucose.

The buffer in the nutrient solution 130 can be an acidic buffer or a basic buffer. The buffer can be used to counteract the buffering effects of ions or substances present in the fluid sample 124 when the fluid sample 124 is composed of a bodily fluid.

The filter 110 comprising the infectious agent 102 can be heated to a temperature of between 30° C. and 40° C. and allowed to incubate for an incubation period 132 in step 1C.

In one embodiment, the filter 110 can be incubated while in the filter housing 108. In another embodiment, the filter 110 can be removed from the filter housing 108 prior to incubation. In some embodiments, the filter 110 can be incubated with the nutrient solution 130. The incubation period 132 can range from 15 minutes to over one hour. In other embodiments, the incubation period 132 can be less than 15 minutes. The incubation period 132 can be adjusted based on the type of infectious agent 102, such as the type of bacteria, fungus, virus, or prion.

The incubation period 132 can also be adjusted based on the amount of the infectious agent 102 present in the fluid sample 124. For example, the incubation period 132 can be increased when the amount of the infectious agent 102 is below a threshold amount. The filter 110 can be allowed to incubate with the nutrient solution 130 in order to promote the proliferation of the infectious agent 102 on the filter surface 126. One advantage of incubating the filter 110 is to increase the sensitivity of the system 100 to small amounts of the infectious agent 102. For example, incubating the filter 110 can allow the system 100 to reduce its level of detection. In one embodiment, the system 100 can detect as few as 500 bacteria per milliliter. In other embodiments, the system 100 can detect fewer than 500 bacteria per milliliter. In further embodiments, the system 100 can detect $10^4$ bacteria per milliliter.

After incubating the filter 110, the same fluid delivery device 106 or another fluid delivery device 106 can then be used to expose the filter surface 126 with additional nutrient solution 130 in step 1D. One advantage of exposing the filter 110 with the additional nutrient solution 130 is to prevent the filter housing 108, the filter 110, or the environment housing the infectious agent 102 from becoming overly acidified as a result of cellular activity, cellular metabolism, or growth undertaken by the infectious agent 102. For example, the filter housing 108 or the filter 110 comprising the infectious agent 102 can become overly acidified as result of the infectious agent 102 undergoing cellular metabolism or growth.

As illustrated in the example embodiment shown in FIG. 1, the effluent or outflow from the exposure step of step 1D can be introduced or applied to one or more of the sensors 116 disposed on the substrate 112. This effluent or outflow can be referred to as a sample effluent 134.

The sample effluent 134 can be introduced to one or more of the sensors 116 disposed on the substrate 112 through the opening 128 in the filter housing 108. The opening 128 can include a channel, a capillary, a tube, or a combination thereof. The sample effluent 134 can be sampled from the nutrient solution 130 exposed to the filter 110. The sample effluent 134 can also be separated from the infectious agent 102 on the filter surface 126 as the sample effluent 134 flows through the filter 110 on to the sensors 116. In these embodiments, the infectious agent 102 can be kept separate or prevented from contacting any portion of the sensors 116 disposed on the substrate 112.

The sample effluent 134 can comprise a solution characteristic 136. The solution characteristic 136 can refer to one or more attributes of the solution making up the sample effluent 134. For example, the solution characteristic 136 can include a concentration of a solute or an absolute number of solutes in solution. The solution characteristic 136 can include an amount or concentration of ions, organic molecules such as amino acids, minerals, or other inorganic compounds in the sample effluent 134.

The solution characteristic 136 can vary as a result of ions, organic molecules, or minerals produced by or attributed to the infectious agent 102 on the filter surface 126. The solution characteristic 136 can be a direct or indirect byproduct of a cellular activity undertaken by the infectious agent 102 such as cell metabolism or cell growth. In one embodiment, the sample effluent 134 can comprise hydrogen ions ($H^+$) as a byproduct of bacterial cell metabolism or growth. In other embodiments, the sample effluent 134 can comprise adenosine triphosphate (ATP), carbon dioxide ($CO_2$), lactic acid, carbonic acid, nitrates ($NO_3^-$), or a combination thereof produced by or attributed to the infectious agent 102.

After introducing the sample effluent 134 to the sensors 116, the same fluid delivery device 106 or another fluid delivery device 106 can be used to introduce an anti-infective 104 to the filter surface 126 comprising the infectious agent 102 in step 1E. In the example embodiment shown in FIG. 1, the anti-infective 104 can be mixed with additional nutrient solution 130 and the filter surface 126 comprising the infectious agent 102 can be exposed to additional nutrient solution 130. In other embodiments, the anti-infective 104 can be introduced to the filter surface 126 separate from the nutrient solution 130.

The anti-infective 104 can comprise a bacteriostatic anti-infective, a bactericidal anti-infective, an anti-fungal anti-infective, an antiviral anti-infective, a prion inhibitor, or a combination thereof. In certain embodiments, the bacteriostatic anti-infective can comprise β-lactams, Aminoglycosides, Ansamycins Glycopeptides, Lipopeptides, Quinolones, Streptogramins, or any combination thereof. The bactericidal anti-infective can comprise Chloramphenicols, Macrolides, Oxazolidinones, Sulfonamides, Tetracyclines, any combination thereof, or future derivations thereof.

In another embodiment, the anti-infective 104 can be a bacterial growth inhibitor or stimulator. The bacterial growth inhibitor or stimulator can selectively inhibit or promote the growth of gram positive or gram negative bacteria. The bacterial growth inhibitor or stimulator can comprise a dye or a chemical compound or reagent. In some embodiments, the dye can include, but is not limited to, Methylene blue, Bromothymol blue, Eosin B, Safranin O, Crystal violet, or a combination thereof. The chemical compound or reagent can include, but is not limited to, sodium azide, bile salts, sodium chloride, tetrathionate, or a combination thereof. The anti-infective 104 can also comprise a carbon source other than glucose, such as lactose, mannose, glycerol, or citrate to select for certain bacterial species. The bacterial growth inhibitor, the carbon source, or a combination thereof can also be added to the nutrient solution 130.

In the example embodiment shown in FIG. 1, the filter 110 incubated in step 1C can be divided into two separate filters 110 with each filter 110 having the infectious agent 102 on the filter surface 126. In this embodiment, nutrient solution 130 containing the anti-infective 104 can be exposed or introduced to one of the filters 110 comprising the infectious agent 102 in step 1D and nutrient solution 130 without the anti-infective 104 can be exposed or introduced to the other filter 110 in step 1E. In one embodiment, step 1D can occur concurrently or near in time with step 1E. In other embodiments, step 1D and step 1E can occur sequentially.

In these embodiments, the sample effluent 134 resulting from the exposure step of step 1D can be introduced to a different sensor 116 than the sensor 116 used to analyze the sample effluent 134 from step 1E. Also, in these embodiments, the sensor 116 receiving the sample effluent 134 containing the anti-infective 104 can be referred to as the active sensor 120 and the sensor 116 receiving the sample effluent 134 without the anti-infective 104 can be referred to as the control sensor 122.

In an alternative embodiment contemplated by the present disclosure, the same filter 110 exposed to the nutrient solution 130 in step 1E can be exposed to a nutrient solution 130 containing the anti-infective 104 at a later point in time. In this embodiment, the sample effluent 134 from the exposure step comprising the anti-infective 104 can also be introduced to the same sensor 116 as the sensor 116 used to measure the non-anti-infective sample effluent 134 in step 1E.

In yet another embodiment contemplated but not shown in FIG. 1, portions of the fluid sample 124 can be divided into multiple filter housings 108 prior to step 1A. In this embodiment, each filter housing 108 can contain a filter 110 comprising infectious agents 102 from the fluid sample 124 disposed on the filter surface 126. Each of the filter housings 108 can be incubated and a variety of nutrient solutions 130, including nutrient solutions 130 lacking in anti-infective 104 or containing different types of anti-infectives 104, can be used to expose the various filters 110. In this embodiment, the sample effluent 134 from the various filter housings 108 can be introduced to different sensors 116 on the substrate 112.

While FIG. 1 illustrates two of the four sensors 116 on the substrate 112 being used to analyze sample effluent 134 from the fluid sample 124, it is contemplated that the substrate 112 can accommodate any number of sensors 116 for receiving the sample effluent 134. For example, the substrate 112 can be a support or housing for a high throughput assay plate such as a 96 well plate, a 192 well plate, or a 384 well plate. In this example, each of the well plates can be in fluid communication with one or more sensors 116. In another embodiment, the sensors 116 can be positioned directly underneath the filter housing 108.

The reader 114, the analyzer 118, or a combination thereof can be configured to monitor an electrical characteristic 800 (see FIG. 8) of the sensors 116 upon introducing the sample effluent 134 to the sensors 116. For example, the reader 114 can monitor the electrical characteristic 800 of the sensors 116 by receiving one or more signals from the analyzer 118 disposed on the substrate 112. In one embodiment, the analyzer 118 can comprise a controller to execute logical commands concerning the detection or comparison of the electrical characteristic 800 of the sensors 116. In other embodiments, the controller can be integrated with the reader 114 or another device coupled to the analyzer 118.

The electrical characteristic 800 can include a current, a voltage, a threshold voltage, a capacitance, a resistance, a noise level, a subthreshold swing, a level of induction, or a combination thereof measured at or near the sensor 116. The reader 114 can be electrically or communicatively coupled to the analyzer 118, the substrate 112, or a combination thereof to monitor the electrical characteristic 800 of the sensors 116 over time. The reader 114 can also be configured to provide a read-out of the electrical characteristic 800 of the sensors 116.

In certain embodiments, the reader 114 can be a mobile device, a handheld device, a tablet device, or a computing device such as a laptop or desktop computer. In other embodiments, the reader 114, the analyzer 118, a combination thereof, or any portion therein can be integrated into an ISFET probe or meter.

In the example embodiment shown in FIG. 1, the analyzer 118, the reader 114, or a combination thereof can monitor the electrical characteristic 800 of the sensors 116, such as the active sensor 120 and the control sensor 122 in step 1F. The analyzer 118, the reader 114, or a combination thereof can monitor the electrical characteristic 800 of the active sensor 120 upon introducing the sample effluent 134 containing the anti-infective 104 to the active sensor 120. In addition, the analyzer 118, the reader 114, or a combination thereof can also monitor the electrical characteristic 800 of the control sensor 122 upon introducing the sample effluent 134 without the anti-infective 104 to the control sensor 122. The analyzer 118, the reader 114, or a combination thereof can compare the electrical characteristic 800 of the active sensor 120 with the electrical characteristic 800 of the control sensor 122 to assess the susceptibility of the infectious agent 102 to the anti-infective 104.

The electrical characteristic 800 of the sensors 116 can differ when the solution characteristic 136 of the sample effluents 134 differ as a result of differences in the concentration or the amount of solutes present in the sample effluents 134. For example, the electrical characteristic 800 of the active sensor 120 and the control sensor 122 can differ when the solution characteristic 136 of the sample effluent 134 introduced to the active sensor 120 differ from the solution characteristic 136 of the sample effluent 134 introduced to the control sensor 122. As a more specific example, the electrical characteristic 800 of the active sensor 120 and the control sensor 122 can differ when the solution characteristic 136 of the sample effluents 134 differ in their pH or differ in the concentration of another ion, an organic molecule, or a combination thereof.

In another embodiment contemplated but not shown in FIG. 1, the analyzer 118, the reader 114, or a combination thereof can monitor the electrical characteristic 800 of one sensor 116 upon introducing the sample effluent 134 without the anti-infective 104 to the sensor 116. In this embodiment, additional nutrient solution 130 comprising the anti-infective 104 can be introduced or exposed to the filter surface 126 comprising the infectious agent 102 and additional sample effluent 134 resulting from this exposure step can be introduced to the sensor 116. The analyzer 118, the reader 114, or a combination thereof can detect any changes in the electrical characteristic 800 of the sensor 116 after introducing the additional sample effluent 134 to the sensor 116. The analyzer 118, the reader 114, or a combination thereof can then assess the susceptibility of the infectious agent 102 to the anti-infective 104 using any detected changes in the electrical characteristic 800 of the sensor 116.

In this embodiment, the change in the electrical characteristic 800 of the sensor 116 can indicate a change in the solution characteristic 136 of the sample effluent 134 introduced to the sensor 116. For example, the change in the solution characteristic 136 of the sample effluent 134 can indicate a change in the concentration of an ion, an organic molecule, or a combination thereof in the sample effluent 134. As a more specific example, the change in the solution characteristic 136 of the sample effluent 134 can be a change in the pH of the sample effluent 134.

In these and other embodiments, the analyzer 118, the reader 114, or a combination thereof can assess the susceptibility of the infectious agent 102 to the anti-infective 104 within a detection period 138. In one embodiment, the detection period 138 can range from 60 minutes to 240 minutes. In another embodiment, the detection period 138 can be less than 60 minutes. In yet another embodiment, the detection period 138 can be greater than 240 minutes.

The reader 114 can produce an output signal 808 (see FIG. 8) assessing the susceptibility of the infectious agent 102. In one embodiment, the output signal 808 can be an electrical signal. In this embodiment, the output signal 808 can be rendered as a graphic, such as a text string, a number, a symbol, or a combination thereof on a display unit of the reader 114. In another embodiment, the output signal 808 can be an audio signal.

The analyzer 118, the reader 114, or a combination thereof can assess the susceptibility of the infectious agent 102 to the anti-infective 104 as a binary assessment or a gradated or tiered assessment. In one embodiment, the analyzer 118, the reader 114, or a combination thereof can assess the susceptibility of the infectious agent 102 as either resistant or non-resistant to the anti-infective 104. In this embodiment, the system 100 can introduce a set amount of the anti-infective 104 to the nutrient solution 130 and the reader 114 or the analyzer 118 can assess the susceptibility of the infectious agent 102 as either resistant or non-resistant based on any detected changes in the electrical characteristic 800 of one sensor 116 or any detected differences in the electrical characteristic 800 of the active sensor 120 and the control sensor 122.

For example, the reader 114, the analyzer 118, or a combination thereof can assess the susceptibility of the infectious agent 102 as resistant to the anti-infective 104 when the analyzer 118 detects a change in the electrical characteristic 800 of the one sensor 116 even after anti-infective 104 is introduced to the filter surface 126 comprising the infectious agent 102. Also, for example, the reader 114, the analyzer 118, or a combination thereof can assess the susceptibility of the infectious agent 102 as not resistant to the anti-infective 104 when the analyzer 118 fails to detect a change in the electrical characteristic 800 of the one sensor 116 when anti-infective 104 is introduced to the filter surface 126 comprising the infectious agent 102. Moreover, the reader 114, the analyzer 118, or a combination thereof can assess the susceptibility of the infectious agent 102 as not resistant to the anti-infective 104 when the analyzer 118 fails to detect a statistically significant change or a change in the electrical characteristic 800 of the one sensor 116 exceeding a threshold value.

As another example, the reader 114, the analyzer 118, or a combination thereof can assess the susceptibility of the infectious agent 102 as resistant to the anti-infective 104 when the analyzer 118 or the reader 114 fails to detect a statistically significant difference between the electrical characteristic 800 of the active sensor 120 and the control sensor 122. More specifically, this statistically significant difference in the electrical characteristic 800 can be a difference exceeding a threshold value. In this example, the system 100 can introduce the sample effluent 134 from the nutrient solution 130 comprising the anti-infective 104 to the active sensor 120 and the sample effluent 134 free from anti-infective 104 to the control sensor 122. In addition, the reader 114, the analyzer 118, or a combination thereof can assess the susceptibility of the infectious agent 102 as not resistant to the anti-infective 104 when the reader 114 or the analyzer 118 detects a statistically significant difference between the electrical characteristic 800 of the active sensor 120 and the control sensor 122 over time.

In other embodiments, the reader 114, the analyzer 118, or a combination thereof can assess the level of susceptibility of the infectious agent 102 on a gradated or tiered scale. For example, the reader 114 can assess the susceptibility of the infectious agent 102 as being resistant, mildly susceptible, or susceptible to the anti-infective 104. In these embodiments, anti-infectives 104 of different concentrations can be introduced to the filter surface 126 comprising the infectious agent 102 to assess the level of susceptibility of the infectious agent 102 to the anti-infective 104.

As a more specific example, when only one sensor 116 is used to assess the level of susceptibility of the infectious agent 102, the system 100 can introduce larger amounts of the anti-infective 104 to the filter surface 126 over time and monitor the effects of the additional anti-infective 104 on the electrical characteristic 800 of the sensor 116 over such a time period. As another example, when multiple active sensors 120 are disposed on the substrate 112, the system 100 can introduce differing amounts of the anti-infective 104 to different active sensors 120 simultaneously or over time and the reader 114, the analyzer 118, or a combination thereof can compare the electrical characteristic 800 of the various active sensors 120 with the control sensor 122 to assess the level of susceptibility of the infectious agent 102 to the anti-infective 104.

While three categories of susceptibility are discussed in the section above, it should be understood by one of ordinary skill in the art that four or greater categories of susceptibility can be used to assess the level of susceptibility of the infectious agent 102 to the anti-infective 104.

Figure 2:
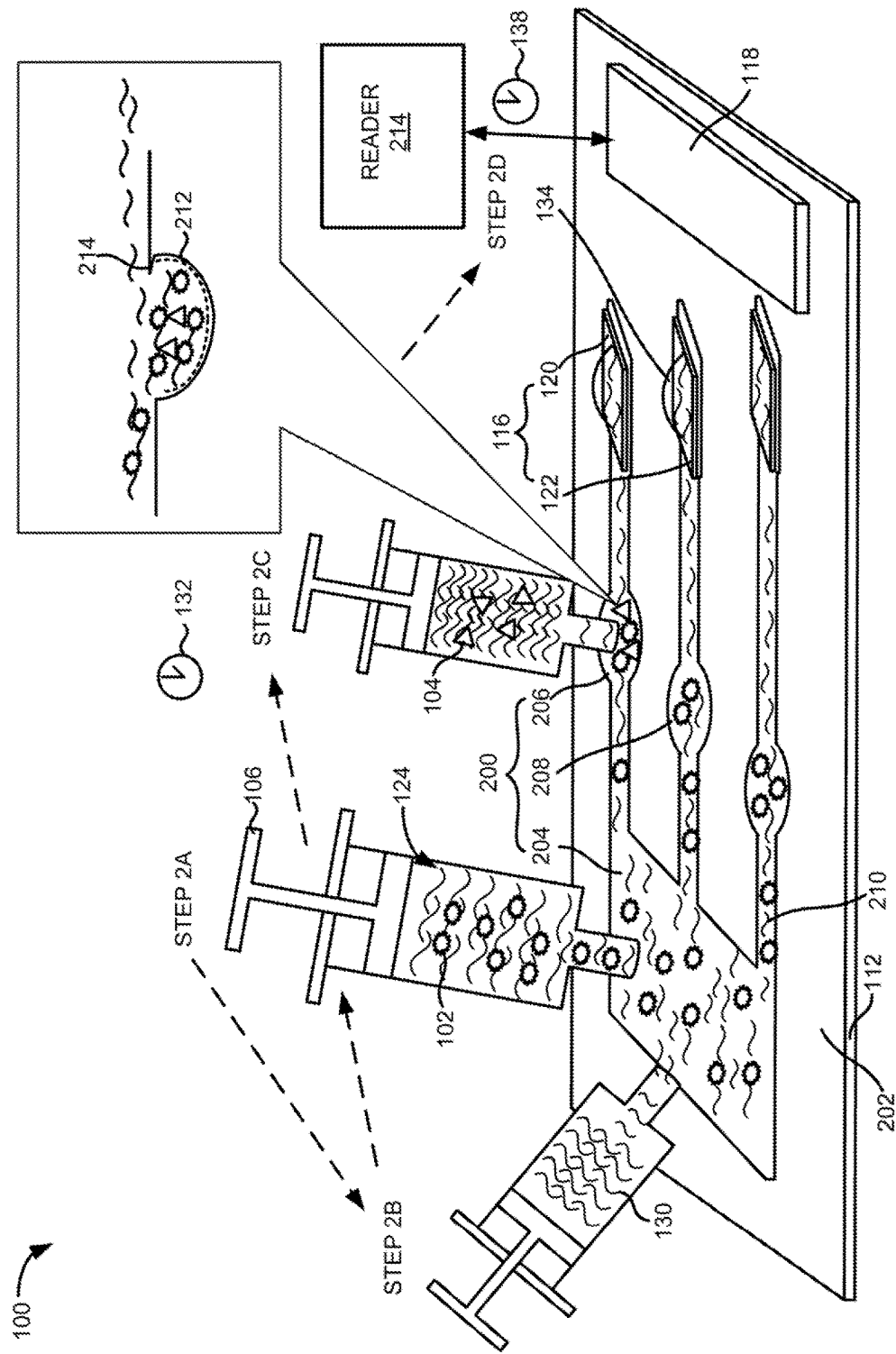
FIG. 2 illustrates another embodiment of the system for detecting a susceptibility of an infectious agent to one or more anti-infectives.

FIG. 2 illustrates another embodiment of the system 100 for detecting or assessing the susceptibility of an infectious agent 102 to an anti-infective 104. The system 100 can comprise the fluid delivery device 106, the substrate 112 comprising substrate wells 200, and the reader 114. The substrate 112 can have one or more sensors 116 disposed on a substrate surface 202. The system 100 can also include the analyzer 118. In the embodiment shown in FIG. 2, the analyzer 118 can be disposed on the substrate surface 202. In other embodiments, the analyzer 118 can be a standalone unit or device coupled to the substrate 112.

The sensors 116 can include one or more active sensors 120, one or more control sensors 122, or a combination thereof disposed on the substrate surface 202. As illustrated in the embodiment shown in FIG. 2, the active sensors 120 and control sensors 122 can be disposed on one side of the substrate 112. In other embodiments not shown in FIG. 2, the active sensors 120 and the control sensors 122 can be disposed on different sides of the substrate 112 or on different substrates. For example, FIG. 2 shows the substrate 112 having three sensors 116; however, it is contemplated that the substrate 112 can comprise any number of sensors 116. In one embodiment, at least one of the sensors 116 can be ISFET.

The substrate wells 200 can include a sample well 204, one or more active wells 206, one or more control wells 208, or a combination thereof. The sample well 204, the one or more active wells 206, the one or more control wells 208, or a combination thereof can be fluidly coupled to or be in fluid communication with one another through substrate channels 210. The substrate channels 210 can include tubes, capillaries, microfluidic channels, indentations, or holes disposed on or inside the substrate 112.

The substrate wells 200 including the sample well 204, the active well 206, the control wells 208, or a combination thereof can be divots, indentations, or openings on the surface of the substrate 112. In another embodiment, the substrate wells 200 can be enclosed spaces within the substrate 112. In other embodiments, the substrate wells 200 can be receptacles or cartridges coupled to the substrate 112. The substrate wells 200 can also be fluidly coupled to or be in fluid communication with the sensors 116 through the substrate channels 210.

As illustrated in FIG. 2, the fluid delivery device 106 can deliver or inject the fluid sample 124 into the sample well 204 in step 2A. The fluid sample 124 can comprise the infectious agent 102.

In another embodiment not shown in FIG. 2, a stimulus solution can be added to the fluid sample 124 before introducing the fluid sample 124 to the filter 110. The stimulus solution can be a nutrient or growth solution. The stimulus solution can have a different composition than the nutrient solution 130. The stimulus solution can be a super nutrient solution.

In an alternative embodiment not shown in FIG. 2, the fluid sample 124 can be pre-filtered in a step before step 2A. This pre-filtering step can involve filtering the fluid sample 124 using the filter 110, a microfluidic filter, or a combination thereof to filter out other larger cellular components including blood cells or epithelial cells from the fluid sample 124.

The same fluid delivery device 106 or another fluid delivery device 106 can also be used to deliver or inject the nutrient solution 130 to the sample well 204 in step 2B. The fluid delivery device 106 can continuously or periodically introduce or expose the substrate surface 202 of the sample well 204 with the nutrient solution 130. In one embodiment, the nutrient solution 130 can be composed of a buffer containing bacto-tryptone, yeast extract, sodium chloride and any combinations thereof. In another embodiment the nutrient solution can include a growth inducer. The growth inducer can be selected from the group consisting of a carbon-based inducer, a nitrogen-based inducer, a mineral, a trace element, a biological growth factor, or any combination thereof. For example, the growth inducer can include but is not limited to glucose, ammonia, magnesium, or a combination thereof. For example, the nutrient solution 130 can be comprised of Tryptone, yeast extract, NaCl, and glucose.

The flow of the nutrient solution 130 can carry or deliver the infectious agent 102 in the sample well 204 to the active well 206, the control well 208, or a combination thereof. For example, the sample well 204, the active well 206, the control well 208, or a combination thereof can be shaped as a hemisphere having a rounded bottom, a cuboid having a flat or planar bottom, a cone, a frustoconical, a hyperboloid, or a combination thereof. The entire substrate 112 can be heated to a temperature between 30° C. to 40° C. when the infectious agent 102 is in the active well 206, the control well 208, or a combination thereof and allowed to incubate for the incubation period 132. The substrate 112 can be allowed to incubate in order to promote the proliferation, metabolism, or growth of the infectious agent 102 in the active wells 206, the control wells 208, or a combination thereof.

The substrate wells 200, including the sample well 204, the active well 206, the control well 208, or a combination thereof, can be covered by a well coating 212. The well coating 212 can cover or coat the bottom or sides of the wells. The well coating 212 can include an anti-buffer coating such as an acidic coating or a basic coating.

The well coating 212 can also be a trapping coating configured to trap the infectious agent 102 in the active wells 206, the control wells 208, or a combination thereof. For example, the well coating 212 can be an extracellular matrix comprising proteins such as fibronectin, collagen, laminin, osteopontin, poly-D-lysine, or a combination thereof. The well coating 212 can also be a charged coating such as an amine surface, a carboxyl surface, a charged peptide surface, or a combination thereof. The well coating 212 can also be an oxygen or nitrogen containing surface. The well coating 212 can also be a polyurethane surface.

The active wells 206, the control wells 208, or a combination thereof can have a physical barrier 214. The physical barrier 214 can be a physical feature or design of the well for trapping or isolating the infectious agent 102 in the active well 206, the control well 208, or a combination thereof. For example, the physical barrier 214 can be an overhang or lip protruding from a downstream section of the active well 206, the control well 208, or a combination thereof. As another example, the physical barrier 214 can be a sloping surface of the active well 206, the control well 208, or a combination thereof. In another embodiment contemplated but not shown in FIG. 2, the physical barrier 214 can be the filter 110 disposed at an opening of the active well 206, the control well 208, or a combination thereof downstream from the sample well 204.

Although the example embodiment in FIG. 2 shows the physical barrier 214 as a feature of the substrate wells 200, the physical barrier 214 can also be a feature of the substrate channels 210. For example, the substrate channels 210 can be microfluidic channels, which narrow to a width or diameter which prevent the infectious agent 102 from proceeding down the substrate channels 210 toward the sensors 116. In this example embodiment, the substrate 112 can act as a microfluidic chip or lab-on-chip (LOC).

The well coating 212, the physical barrier 214, or a combination thereof can be included as part of the system 100 to prevent or stop the infectious agent 102 from contacting or reaching the sensors 116. In another embodiment contemplated but not shown in FIG. 2, an electrical or magnetic component can be used to trap or isolate the infectious agent 102 in the active well 206, the control well 208, or a combination thereof.

The nutrient solution 130 delivered in step 2B or additional nutrient solution 130 can be continuously or periodically delivered or injected into the sample well 204, the active well 206, the control well 208, or a combination thereof until the infectious agent 102 is carried or delivered into one or more active wells 206, control wells 208, or a combination thereof. The active wells 206, the control wells 208, or a combination thereof can comprise one or more openings, physical features, geometries, or device features which allow fluid or supernatant in the active wells 206, the control wells 208, or a combination thereof to evacuate or exit the wells into one or more substrate channels 210. The fluid or supernatant sampled or separated from the infectious agent 102 in the active wells 206, the control wells 208, or a combination thereof can be referred to as the sample effluent 134.

As illustrated in the example embodiment shown in FIG. 2, the sample effluent 134 can be introduced, carried, or delivered to one or more of the sensors 116 disposed on the substrate 112. The sample effluent 134 can comprise a solution characteristic 136. The solution characteristic 136 can include an amount or concentration of ions, organic molecules such as amino acids, minerals, or other inorganic compounds in the sample effluent 134.

The solution characteristic 136 can vary as a result of ions, organic molecules, or minerals produced by or attributed to the infectious agent 102 in the active wells 206, the control wells 208, or a combination thereof. The solution characteristic 136 can be a direct or indirect byproduct of a cellular activity undertaken by the infectious agent 102 such as cell metabolism or cell growth. The sample effluent 134 can comprise $H^+$, ATP, $CO_2$, lactic acid, carbonic acid, $NO_3^-$, or a combination thereof.

The substrate channels 120 can deliver or introduce sample effluent 134 from one or more active wells 206 to one or more active sensors 120. In addition, separate substrate channels 120 can deliver or introduce sample effluent 134 from one or more control wells 208 to one or more control sensors 122.

After or prior to incubating the substrate 112, the same fluid delivery device 106 or another fluid delivery device 106 can be used to introduce an anti-infective 104 to the active wells 206 in a step 2C. In the example embodiment shown in FIG. 2, the anti-infective 104 can be mixed with additional nutrient solution 130 and the active wells 206 comprising the infectious agent 102 can be exposed to additional nutrient solution 130 comprising the anti-infective 104. In other embodiments, the anti-infective 104 can be introduced to the active wells 206 separate from the nutrient solution 130.

In the example embodiment shown in FIG. 2, nutrient solution 130 containing the anti-infective 104 can be delivered or introduced to the active well 206 comprising the infectious agent 102 while nutrient solution 130 lacking the anti-infective 104 can be delivered or introduced to the control well 208 also comprising the infectious agent 102. In these embodiments, the sample effluent 134 flowing from the active well 206 can be introduced to the active sensor 120 and the sample effluent 134 flowing from the control well 208 can be introduced to the control sensor 122.

In an alternative embodiment contemplated but not shown in FIG. 2, one active well 206 can initially be exposed to nutrient solution 130 lacking in anti-infective 104 and the sample effluent 134 flowing from the active well 206 can be introduced to a sensor 116. In this embodiment, the same active well 206 can be exposed at a later time with nutrient solution 130 comprising the anti-infective 104. By doing so, the sample effluent 134 from this second exposure step can be introduced to the same sensor 116 as the sensor 116 used to measure the non-anti-infective sample effluent 134.

While FIG. 2 illustrates two of the three sensors 116 on the substrate 112 being used to analyze sample effluent 134 from the fluid sample 124, it is contemplated that the substrate 112 can accommodate any number of sensors 116 for receiving the sample effluent 134. For example, the substrate 112 can be a support or housing for a high throughput assay plate such as a 96-well plate, a 192-well plate, or a 384-well plate. In this example, each of the well plates can be in fluid communication with at least one sensor 116.

The reader 114, the analyzer 118, or a combination thereof can be configured to monitor the electrical characteristic 800 of the sensors 116 upon introducing the sample effluent 134 to the sensors 116. For example, the reader 114 can monitor the electrical characteristic 800 of the sensors 116 by receiving one or more signals from the analyzer 118 disposed on the substrate 112.

In the example embodiment shown in FIG. 2, the analyzer 118, the reader 114, or a combination thereof can monitor the electrical characteristic 800 of the sensors 116, such as the active sensor 120 and the control sensor 122 in step 2D. The analyzer 118, the reader 114, or a combination thereof can monitor the electrical characteristic 800 of the active sensor 120 upon introducing the sample effluent 134 from the active well 206 to the active sensor 120. In addition, the analyzer 118, the reader 114, or a combination thereof can also monitor the electrical characteristic 800 of the control sensor 122 upon introducing the sample effluent 134 from the control well 208 to the control sensor 122. The analyzer 118, the reader 114, or a combination thereof can compare the electrical characteristic 800 of the active sensor 120 with the electrical characteristic 800 of the control sensor 122 to assess the susceptibility of the infectious agent 102 to the anti-infective 104.

The electrical characteristic 800 of the sensors 116 can differ when the solution characteristic 136 of the sample effluents 134 differ as a result of differences in the concentration or the amount of solutes present in the sample effluents 134. For example, the electrical characteristic 800 of the active sensor 120 and the control sensor 122 can differ when the solution characteristic 136 of the sample effluent 134 introduced to the active sensor 120 differ from the solution characteristic 136 of the sample effluent 134 introduced to the control sensor 122.

In another embodiment contemplated but not shown in FIG. 2, the analyzer 118, the reader 114, or a combination thereof can monitor the electrical characteristic 800 of one sensor 116 upon introducing the sample effluent 134 without the anti-infective 104 to the sensor 116. In this embodiment, additional nutrient solution 130 comprising the anti-infective 104 can be delivered or exposed to the same sensor 116 and additional sample effluent 134 resulting from this exposure step can be introduced to the sensor 116. The analyzer 118, the reader 114, or a combination thereof can detect any changes in the electrical characteristic 800 of the sensor 116 after introducing the additional sample effluent 134 to the sensor 116. The analyzer 118, the reader 114, or a combination thereof can then assess the susceptibility of the infectious agent 102 to the anti-infective 104 using any detected changes in the electrical characteristic 800 of the sensor 116.

In this embodiment, the change in the electrical characteristic 800 of the sensor 116 can indicate a change in the solution characteristic 136 of the sample effluent 134 introduced to the sensor 116. For example, the change in the solution characteristic 136 of the sample effluent 134 can indicate a change in the concentration of an ion, an organic molecule, or a combination thereof in the sample effluent 134. As a more specific example, the change in the solution characteristic 136 of the sample effluent 134 can be a change in the pH of the sample effluent 134.

In these and other embodiments, the analyzer 118, the reader 114, or a combination thereof can assess the susceptibility of the infectious agent 102 to the anti-infective 104 within the detection period 138.

The reader 114 can also produce the output signal 808 assessing the susceptibility of the infectious agent 102. The analyzer 118, the reader 114, or a combination thereof can assess the susceptibility of the infectious agent 102 to the anti-infective 104 as the binary assessment or the gradated or tiered assessment.

For example, the reader 114, the analyzer 118, or a combination thereof can assess the susceptibility of the infectious agent 102 as resistant to the anti-infective 104 when the analyzer 118 detects a change in the electrical characteristic 800 of the active sensor 120 even after anti-infective 104 is introduced to the active well 206 fluidly coupled to the active sensor 120. Also, for example, the reader 114, the analyzer 118, or a combination thereof can assess the susceptibility of the infectious agent 102 as not resistant to the anti-infective 104 when the analyzer 118 fails to detect a change in the electrical characteristic 800 of the active sensor 120 when anti-infective 104 is introduced to the active well 206 fluidly coupled to the active sensor 120. Moreover, the reader 114, the analyzer 118, or a combination thereof can assess the susceptibility of the infectious agent 102 as not resistant to the anti-infective 104 when the analyzer 118 fails to detect a statistically significant change or a change in the electrical characteristic 800 of the active sensor 120 exceeding a threshold value.

As another example, the reader 114, the analyzer 118, or a combination thereof can assess the susceptibility of the infectious agent 102 as resistant to the anti-infective 104 when the analyzer 118 or the reader 114 fails to detect a statistically significant difference between the electrical characteristic 800 of the active sensor 120 and the control sensor 122. More specifically, a statistically significant difference in the electrical characteristic 800 can be a difference exceeding a threshold value. In this example, the system 100 can introduce the sample effluent 134 from the active well 206 to the active sensor 120 and the sample effluent 134 from the control well 208 to the control sensor 122. In addition, the reader 114, the analyzer 118, or a combination thereof can assess the susceptibility of the infectious agent 102 as not resistant to the anti-infective 104 when the reader 114 or the analyzer 118 detects a statistically significant difference between the electrical characteristic 800 of the active sensor 120 and the control sensor 122.

In other embodiments, the reader 114, the analyzer 118, or a combination thereof can assess the level of susceptibility of the infectious agent 102 on a gradated or tiered scale. For example, the reader 114, the analyzer 118, or a combination thereof can assess the susceptibility of the infectious agent 102 as being resistant, mildly susceptible, or susceptible to the anti-infective 104. In these embodiments, anti-infectives 104 of different concentrations can be introduced to different active wells 206 comprising the infectious agent 102 to assess the level of susceptibility of the infectious agent 102 to the anti-infective 104.

As an example, when only one sensor 116 is used to assess the level of susceptibility of the infectious agent 102, the system 100 can introduce larger amounts of the anti-infective 104 to the active well 206 over time and monitor the effects of the additional anti-infective 104 on the electrical characteristic 800 of the active sensor 120 fluidly coupled to the active well 206 over such a time period. As another example, when multiple active sensors 120 are disposed on the substrate 112, the system 100 can introduce differing amounts of the anti-infective 104 to different active wells 206 and the reader 114, the analyzer 118, or a combination thereof can compare the electrical characteristic 800 of the various active sensors 120 with one or more control sensors 122 to assess the level of susceptibility of the infectious agent 102 to the anti-infective 104.

Figure 3:
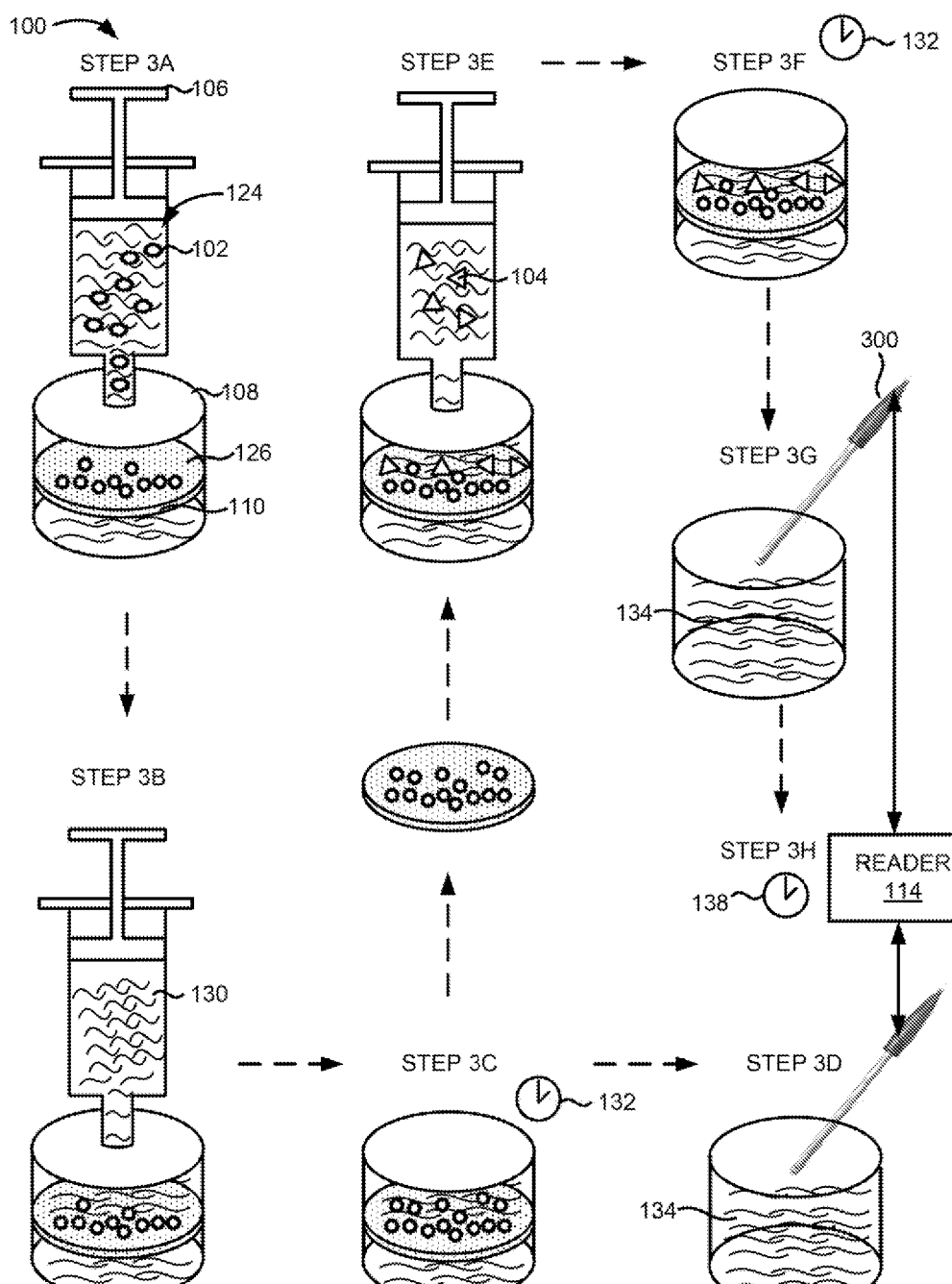
FIG. 3 illustrates another embodiment of the system for detecting a susceptibility of an infectious agent to one or more anti-infectives.

FIG. 3 illustrates another embodiment of the system 100 for detecting or assessing the susceptibility of an infectious agent 102 to an anti-infective 104. The system 100 can comprise the fluid delivery device 106, the filter housing 108 containing the filter 110, and a sensor device 300. In one embodiment, the sensor device 300 can be a handheld ISFET meter or probe.

As illustrated in FIG. 3, the fluid delivery device 106 can deliver or inject the fluid sample 124 into the filter housing 108 in step 3A. The fluid sample 124 can comprise the infectious agent 102. In the example embodiment shown in FIG. 3, the fluid delivery device can be a pump. For example, the fluid delivery device 106 can be a syringe pump, a pneumatic pump, or a hydraulic pump.

In other embodiments not shown in FIG. 3, the fluid delivery device 106 can be an injection cartridge, a microfluidic device, a pipette, a reaction tube, a capillary, a test tube, a combination thereof, or a portion therein.

The filter housing 108 can be a container or vessel configured to secure or enclose the filter 110. The filter housing 108 can be a container or vessel configured to secure or enclose the filter 110. The filter housing 108 can also be a protective chamber. The protective chamber can be an electrically isolated environment, a temperature controlled chamber, and/or a light controlled chamber. For example, the filter housing 108 can be a housing of a syringe filter.

The filter 110 can be a non-clogging filter. The filter 110 can have a non-clogging filter surface. The filter 110 can also have filter pores of sequentially smaller pore size. For example, the filter 110 can have larger filter pores at the top of the filter and progressively smaller filters pores toward the bottom of the filter 110. Although not shown in FIG. 3, it is contemplated by this disclosure that the filter 110 can refer to a plurality of filters in a stacked arrangement.

The filter 110 can be a mesh or matrix for isolating or separating the infectious agent 102 or other molecules or cells from the supernatant of the fluid sample 124.

The filter 110 can comprise a filter surface 126. The filter surface 126 can be the portion of the filter 110 used to isolate or trap the infectious agent 102. The filter surface 126 can include an external surface, an internal surface extending into the filter 110, or a combination thereof. Although not shown in FIG. 3, the filter housing 108 can have at least one opening 128 to allow fluid or supernatant from the fluid sample 124 to evacuate the filter housing 108. For example, step 3A can include the additional step of discarding the fluid or supernatant from the fluid sample 124 through the opening 128 after isolating the infectious agent 102 on the filter surface 126.

In another embodiment not shown in FIG. 3, a stimulus solution can be added to the fluid sample 124 before introducing the fluid sample 124 to the filter 110. The stimulus solution can be a nutrient or growth solution. The stimulus solution can have a different composition than the nutrient solution 130. The stimulus solution can be a super nutrient solution.

In an alternative embodiment not shown in FIG. 3, the fluid sample 124 can be pre-filtered in a step before step 3A. This pre-filtering step can involve filtering the fluid sample 124 using another instance of the filter 110, a microfluidic filter, or a combination thereof to filter out other larger cellular components including blood cells or epithelial cells from the fluid sample 124 when the fluid sample 124 is composed of a bodily fluid or sample.

The same fluid delivery device 106 or another fluid delivery device 106 can also be used to deliver or inject a nutrient solution 130 to the filter housing 108 in step 3B. The fluid delivery device 106 can continuously or periodically introduce or expose the nutrient solution 130 to the filter surface 126 containing the infectious agent 102. In one embodiment, the nutrient solution 130 can be composed of Tryptone, yeast extract, NaCl, glucose, and the buffer.

The filter housing 108 comprising the nutrient solution 130, the filter, and the infectious agent 102 can be heated to a temperature of around 37° C. and allowed to incubate for an incubation period 132 in a step 3C. The incubation period 132 can range from 15 minutes to one hour. In other embodiments, the incubation period 132 can be less than 15 minutes. The incubation period 132 can be adjusted based on the type of infectious agent 102.

The incubation period 132 can also be adjusted based on the amount of the infectious agent 102 present in the fluid sample 124. For example, the incubation period 132 can be increased when the amount of the infectious agent 102 is below a threshold amount. The filter 110 can be allowed to incubate with the nutrient solution 130 in order to promote the metabolism of the infectious agent 102 on the filter 110. Furthermore, by monitoring the rate at which metabolites are produced using the sensor herein described, it is possible to identify the infectious agent, as different infectious agents have characteristic rates of multiplication and metabolism. There is an additional feature hereby disclosed, namely providing different nutrients to the infectious agents over time while monitoring the rate of production of various metabolites using the sensor herein described in order to further identify the infectious agent.

After incubating the filter housing 108, the filter 110 comprising the infectious agent 102 can be separated from a solution representing the leftover nutrient solution 130 in the filter housing 108. This solution can be referred to as the sample effluent 134. The sensor device 300 can then be introduced or inserted in to the sample effluent 134 in step 3D to determine the solution characteristic 136 of the sample effluent 134. In another embodiment contemplated but not shown in FIG. 3, the sample effluent 134 can be evacuated or removed from the filter housing 108 through an opening in the filter housing 108 into another container or vessel. The sensor device 300 can then be used to determine the solution characteristic 136 of the sample effluent 134 in this other container or vessel.

The solution characteristic 136 can refer to one or more attributes of the solution making up the sample effluent 134. For example, the solution characteristic 136 can include a concentration of a solute or an absolute number of solute molecules in solution. The solution characteristic 136 can include an amount or concentration of ions, organic molecules such as amino acids, minerals, or other inorganic compounds in the sample effluent 134.

The solution characteristic 136 can vary as a result of ions, organic molecules, or minerals produced by or attributed to the infectious agent 102 on the filter 110. The solution characteristic 136 can be a direct or indirect byproduct of a cellular activity undertaken by the infectious agent 102 such as cell metabolism or cell growth. In one embodiment, the sample effluent 134 can comprise hydrogen ions ($H^+$) as a byproduct of bacterial cell metabolism or growth. In other embodiments, the sample effluent 134 can comprise adenosine triphosphate (ATP), carbon dioxide ($CO_2$), lactic acid, carbonic acid, nitrates ($NO_3^-$), a combination thereof, or any other metabolic byproduct produced by or attributed to the infectious agent 102.

After step 3C, the filter 110 comprising the infectious agent 102 can be removed from the filter housing 108 containing the sample effluent 134 and placed into a new filter housing 108. The same fluid delivery device 106 or another fluid delivery device 106 can then be used to introduce an anti-infective 104 to the new filter housing 108 containing the filter 110 in a step 3E. In an alternative embodiment, step 3E can involve using the same fluid delivery device 106 or another fluid delivery device 106 to introduce an anti-infective 104 to the filter housing 108 from step 3C after the sample effluent 134 has been evacuated or removed from the opening of the filter housing 108.

In the example embodiment shown in FIG. 3, the anti-infective 104 can be mixed with additional nutrient solution 130 and the filter 110 comprising the infectious agent 102 can be exposed to additional nutrient solution 130. In other embodiments, the anti-infective 104 can be introduced to the filter 110 separate from the nutrient solution 130.

After introducing the anti-infective 104 to the filter housing 108, the filter housing 108 comprising the nutrient solution 130, the filter 110, the anti-infective 104, and the infectious agent 102 can be heated to a temperature of around 37° C. and allowed to incubate for an incubation period 132 in a step 3F.

After incubating the filter housing 108, the filter 110 comprising the infectious agent 102 can be separated from the sample effluent 134. A sensor device 300 can then be introduced or inserted into the sample effluent 134 in step 3G to determine the solution characteristic 136 of the sample effluent 134. In another embodiment contemplated but not shown in FIG. 3, the sample effluent 134 can be evacuated or removed from the filter housing 108 through an opening in the filter housing 108 into another container or vessel. The sensor device 300 can then be used to determine the solution characteristic 136 of the sample effluent 134 in this other container or vessel.

The reader 114 can then be used to compare the solution characteristic 136 of the sample effluent 134 from step 3G with the solution characteristic 136 of the sample effluent 134 from step 3D to assess the susceptibility of the infectious agent 102 to the anti-infective 104 in step 3H. For example, the reader 114 can be used to compare the two solution characteristics 136 over time. The solution characteristic 136 from step 3D and step 3G can differ as a result of differences in the concentration or the amount of solutes present in the sample effluents 134. For example, the solution characteristic 136 can differ in their pH or differ in the concentration of another ion, an organic molecule, or a combination thereof.

The reader 114 can assess the susceptibility of the infectious agent 102 to the anti-infective 104 within a detection period 138. In one embodiment, the detection period 138 can range from 60 minutes to 240 minutes. In another embodiment, the detection period 138 can be less than 60 minutes. In yet another embodiment, the detection period 138 can be greater than 240 minutes.

The reader 114 can produce an output signal 808 assessing the susceptibility of the infectious agent 102. In one embodiment, the output signal 808 can be an electrical signal. In this embodiment, the output signal 808 can be rendered as a graphic, such as a text string, a number, a symbol, or a combination thereof on a display unit of the reader 114. In another embodiment, the output signal 808 can be an audio signal.

The reader 114 can assess the susceptibility of the infectious agent 102 to the anti-infective 104 as a binary assessment or a gradated or tiered assessment. In one embodiment, the reader 114 can assess the susceptibility of the infectious agent 102 as either resistant or non-resistant to the anti-infective 104. In this embodiment, the reader 114 can assess the susceptibility of the infectious agent 102 as either resistant or non-resistant based on any detected differences in the solution characteristic 136.

For example, the reader 114 can assess the susceptibility of the infectious agent 102 as resistant to the anti-infective 104 when the reader 114 fails to detect a statistically significant difference between the solution characteristic 136 from step 3D and the solution characteristic 136 from step 3G over time. A statistically significant difference can refer to a difference exceeding a threshold value. Also, the reader 114 can assess the susceptibility of the infectious agent 102 as sensitive to the anti-infective 104 when the reader 114 detects a statistically significant difference between the solution characteristic 136 from step 3D and the solution characteristic 136 from step 3G over time.

In other embodiments, the reader 114 can assess the level of susceptibility of the infectious agent 102 on a gradated or tiered scale. For example, the reader 114 can assess the susceptibility of the infectious agent 102 as being resistant, mildly susceptible, or susceptible to the anti-infective 104. In these embodiments, anti-infectives 104 of different concentrations can be introduced to the filter housing 108 in step 3E to assess the level of susceptibility of the infectious agent 102 to the anti-infective 104. The reader 114 can compare the solution characteristic 136 of the various sample effluents 134 over time to assess the level of susceptibility of the infectious agent 102 to the anti-infective 104.

Figure 4A:
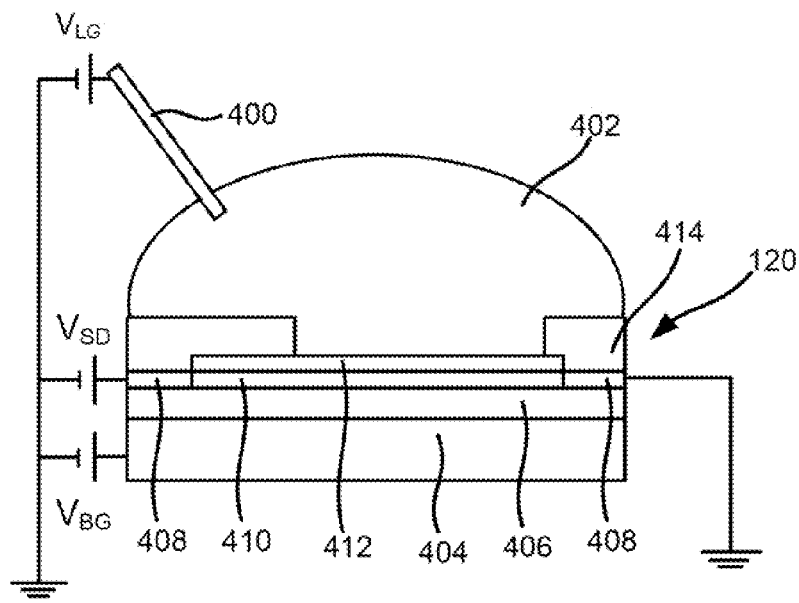
FIG. 4A illustrates a side view of an embodiment of a substrate having an active sensor disposed on the substrate and an external reference.

FIG. 4A illustrates a side view of an active sensor 120. The active sensor 120 can be disposed on a semiconductor layer 404. The active sensor 120 can have an external reference electrode 400 extending into a measured liquid 402 in contact with the active sensor 120. As depicted in FIG. 4A, the active sensor 120 can comprise a semiconductor layer 404 and a base dielectric layer 406. The active sensor 120 can comprise a polymer layer, a metal layer, a metalloid layer, a ceramic layer, an organic semiconductor, a carbon nanotube layer, a graphene layer, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The semiconductor layer 404 can be composed of silicon or an oxide of silicon which allows a voltage to be applied through the semiconductor layer 404 to the sensor channel 410.

The base dielectric layer 406 can be coupled or can be disposed on the semiconductor layer 404 to electrically insulate or isolate each of the sensors 116 from one another. In one embodiment, the base dielectric layer 406 can be composed of an oxide material. In other embodiments, the base dielectric layer 406 can be composed of any other material capable of providing insulation.

In one or more embodiments, the sensors 116 of the system 100, including the active sensor 120, the control sensor 122, or a combination thereof can be fabricated using a complementary metal oxide semiconductor (CMOS) process or a similar process. For example, the active sensor 120, the control sensor 122, or a combination thereof can be integrated CMOS ISFET sensors fabricated from p-type and n-type metal oxide semiconductor field-effect transistors (MOSFETs). In another embodiment, the sensors 116 can be organic field-effect transistors (OFETs).

As depicted in FIG. 4A, the active sensor 120 can comprise sensor contacts 408, a sensor channel 410 in between the sensor contacts 408, a gate dielectric layer 412 coupled to or on top of the sensor channel 410, and an encapsulating layer 414 partially covering the gate dielectric layer 412 of the active sensor 120. The sensor contacts 408 can include a source contact and a drain contact. For example, the sensor contacts 408 can be composed of highly doped p-type material. The sensor channel 410 can act as a bridge between the two sensor contacts 408 and can be composed of any electrically conductive material or coating that allows for electrical communication between the sensor contacts 408.

The gate dielectric layer 412 can be coupled to or disposed on top of the sensor channel 410. In certain embodiments, the gate dielectric layer 412 can be a high-k dielectric layer or a material layer having a high dielectric constant (k). For example, the gate dielectric layer 412 can comprise aluminum oxide, hafnium oxide, titanium oxide, zirconium oxide, yttrium oxide, tantalum oxide, hafnium silicate, zirconium silicate, silicon nitride, aluminum nitride, hafnium nitride, zirconium nitride, or a combination thereof. As a more specific example, the gate dielectric layer 412 can comprise aluminum dioxide, hafnium dioxide, zirconium dioxide, or a combination thereof. In other embodiments, the gate dielectric layer 412 can comprise a silicon dioxide layer.

Any of the sensors 116, including the active sensor 120 and the control sensor 122, can be partially covered by the encapsulating layer 414. The encapsulating layer 414 can be composed of any inert or non-conductive material for protecting the sensor 116 from being exposed to solutes or contaminants in the measured liquid 402 that would damage or degrade the sensor 116.

As depicted in FIG. 4A, the system 100 can also comprise an external reference electrode 400 in liquid communication with the measured liquid 402 and the sensor 116 itself. The measured liquid 402 can refer to any of the sample effluent 134, the nutrient solution 130, the fluid sample 124, a portion therein, or a combination thereof. The fluid sample 124 can be introduced to the sensors 116 from the filter housing 108, the substrate wells 200, or any other fluid delivery device 106. The fluid sample 124 can cover the active sensor 120, the control sensor 122, or a combination thereof when introduced to the sensors 116. In other embodiments, the fluid sample 124 can partially cover or be in liquid communication with the active sensor 120, the control sensor 122, or a combination thereof when introduced to the sensors 116.

The external reference electrode 400 can apply a potential, such as a liquid gate potential, to the measured liquid 402. In one embodiment, the external reference electrode 400 can be a standalone probe or electrode. In other embodiments, the external reference electrode 400 can be coupled to the reader 114, the analyzer 118, or a combination thereof. The external reference electrode 400 can have a stable and well-known internal voltage and can act as a differential noise filter for removing electrical noise from measurements taken by the sensors 116.

In one embodiment, the external reference electrode 400 can be a silver/silver chloride (Ag/AgCl) electrode. In other embodiments, the external reference electrode 400 can be a saturated calomel reference electrode (SCE) or a copper-copper (II) sulfate electrode (CSE).

The system 100 can use the external reference electrode 400 to determine or record a relative change in the electrical characteristic 800 of the active sensor 120 rather than having to ascertain an absolute change. The system 100 can also use the external reference electrode 400 to determine or record a relative difference between the electrical characteristic 800 of the active sensor 120 and the control sensor 122.

A back-gate voltage Vbg can be applied via the silicon substrate. The electrical characterization of ISFETs can be performed by applying a source-drain voltage Vsd to measure the source-drain current Isd. In another embodiment, a liquid gate voltage can be applied to a solution via a reference electrode. The electrical characterization of ISFETs can be performed applying a source-drain voltage Vsd to measure the source-drain current Isd. In another embodiment, a dual-gate approach can be used by applying gate voltages simultaneously to the back gate and to the liquid gate. This allows an operator to tune the device to different working positions, optimizing the sensitivity. The back-gate voltage Vbg is applied to the Si substrate, while the liquid gate voltage Vlg is applied via a reference electrode. At the same time, the liquid potential Vlg can be measured by the reference electrode. When the ion concentration in the solution is changing, the ISFET responds with a change in the electrical characteristic. For example, in case of proton (H+) changes, the protons interact with the oxide surface of the ISFET. This is the expected dependence for an oxide surface exposing hydroxl (—OH) groups to the liquid. The change in surface charge density caused by a pH change is described by the site-binding model, which takes into account that —OH groups can be protonated or deprotonated. This model predicts an approximate linear relation between the surface charge density and the proton concentration. Since the surface charge acts as an additional gate, the ISFET is responding to the additional gate effect.

Figure 4B:
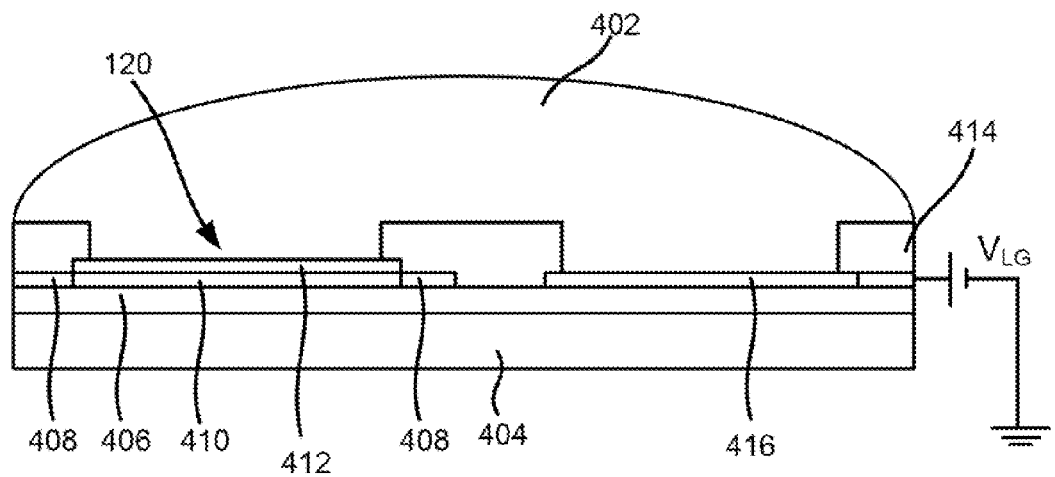
FIG. 4B illustrates a side view of an embodiment of a substrate having the active sensor and an on-chip reference electrode disposed on the substrate.

FIG. 4B illustrates a side view of another embodiment of the semiconductor layer 404 having the active sensor 120 and an on-chip reference electrode 416 disposed on it. The on-chip reference electrode 416 can serve the same purpose as the external reference electrode 400 except fabricated as a chip or sensor on the semiconductor layer 404 or the insulator layer 406. The on-chip reference electrode 416 can be located adjacent to or near the active sensor 120. The on-chip reference electrode 416 can be on the base dielectric layer 406. The on-chip reference electrode 416 can also be partially covered by the encapsulating layer 414. The on-chip reference electrode 416 can apply a liquid gate voltage ($V_{LG}$) to the measured liquid 402.

The on-chip reference electrode 416, the external reference electrode 400, or a combination thereof can be comprised of a metal, a semiconductor material, or a combination thereof. In one embodiment, the control sensor 122 can act as the on-chip reference electrode 416. The metal of the on-chip reference electrode 416 can be covered by an oxide layer, a silane layer, or a combination thereof. Since metals or other materials used to fabricate such reference electrodes can often have an inhibitory or harmful effect on the infectious agents 102 under investigation, one advantage of the methods and systems 100 disclosed herein is the separation of the infectious agent 102 from the components of the system 100 in physical or fluid contact with these reference electrodes.

For example, the external reference electrode 400 can be an Ag/AgCl reference electrode. In this example, silver ions or a silver surface making up the external reference electrode 400 can act as an anti-infective agent when placed into contact with certain types of bacteria, fungus, virus, or prion. By separating the sample effluent 134 from the bacteria, fungus, virus, or prion representing the infectious agent 102, the system 100 can prevent false positive or false negative results stemming from the antibacterial effects of the reference electrode on the infectious agent 102 under investigation. For example, the filter 110 or the substrate wells 200 can trap or isolate the infectious agent 102 but permit the nutrient solution 130 or the sample effluent 134 to reach the sensors 116 and the reference electrode.

The on-chip reference electrode 416 can be a transistor with very similar electrical properties as compared to the sensor 116 but with a passivated surface, the so-called reference FET (RFET). The RFET can be an ISFET with a pH-passivating membrane, ion-blocking layers of photoresist material, or other polymers. The on-chip reference electrode 416 can comprise one or more pH-insensitive layers covering an ISFET. Such pH-insensitive layers can include silanes, self-assembled mono layers (SAMs), buffered hydrogels, PVC, parylene, polyACE, or any other chemically inert material. Also a metal, such as Ag or Pt, can be used as a quasi-reference electrode evaporated on the substrate carrier. In another embodiment, the on-chip reference electrode 416 can be a metal combined with a metal salt such as an Ag/AgCl reference electrode.

FIG. 5A illustrates a side view of yet another embodiment of the semiconductor layer 404 having the active sensor 120 and a control sensor 122 disposed on it and the external reference electrode 400 extending into the measured liquid 402 in contact with the active sensor 120 and the control sensor 122. Similar to the active sensor 120, the control sensor 122 can comprise a pair of sensor contacts 408, a sensor channel 410 in between the sensor contacts 408, a gate dielectric layer 412 coupled to or on top of the sensor channel 410, and an encapsulating layer 414 partially covering the gate dielectric layer 412 of the control sensor 122.

The sensor contacts 408 can include a source contact and a drain contact. The sensor channel 410 can act as a bridge between the two sensor contacts 408 and can be composed of any electrically conductive material or coating that allows for electrical communication between the sensor contacts 408.

The gate dielectric layer 412 can be coupled to or disposed on top of the sensor channel 410. In certain embodiments, the gate dielectric layer 412 can be a high-k dielectric layer or a material layer having a high dielectric constant. For example, the gate dielectric layer 412 of the control sensor 122 can comprise aluminum oxide, hafnium oxide, titanium oxide, zirconium oxide, yttrium oxide, tantalum oxide, hafnium silicate, zirconium silicate, or a combination thereof. As a more specific example, the gate dielectric layer 412 can comprise aluminum dioxide, hafnium dioxide, zirconium dioxide, or a combination thereof. In other embodiments, the gate dielectric layer 412 can comprise a silicon dioxide layer.

The encapsulating layer 414 can be composed of any inert or non-conductive material for protecting the control sensor 122 from being exposed to solutes or contaminants in the measured liquid 402 that would damage or degrade the control sensor 122.

In the example embodiment shown in FIG. 5A, the control sensor 122 can comprise a passivation layer 500 coupled to or disposed on the gate dielectric layer 412. The passivation layer 500 can be composed of a polymer layer, a metallic layer, a self-assembled monolayer (SAM), or a combination thereof. The passivation layer 500 can be used to prevent binding of ions or molecules to the surface of the control sensor 122. In other embodiments, the control sensor 122 can be without the passivation layer 500 and the makeup of the control sensor 122 can be identical to the active sensor 120. For example, the passivation layer 500 can be a pH-passivating membrane, an ion-blocking layer, a photoresist material, or any other polymer. In addition, the passivation layer 500 can be a pH-insensitive layer covering an ISFET. Example of pH-insensitive layers include silanes, SAMs, buffered hydrogels, PVC, parylene, polyACE, or a combination thereof.

FIG. 5B illustrates a side view of another embodiment of the semiconductor layer 404 having the active sensor 120, the control sensor 122, and the on-chip reference electrode 416 disposed on it. As shown in FIG. 5B, the on-chip reference electrode 416 can be disposed or located in between the active sensor 120 and the control sensor 122.

Figure 6A:
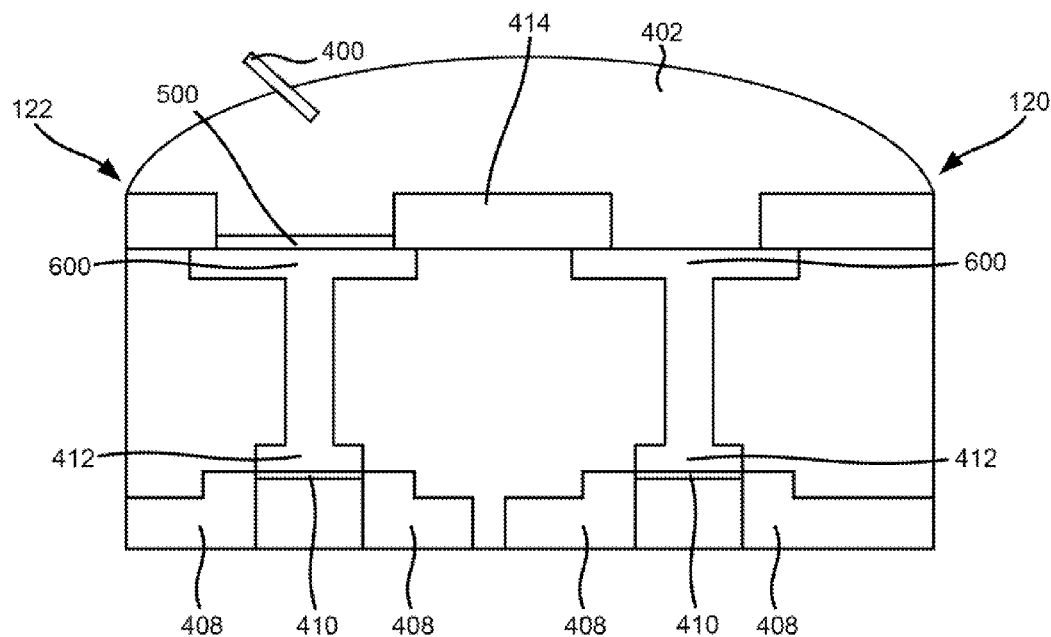
FIG. 6A illustrates a side view of an embodiment of the active sensor and the control sensor each having an extended gate and an external reference electrode.

FIG. 6A illustrates a side view of an embodiment of the active sensor 120 and the control sensor 122 each having an extended gate 600. The extended gate 600 can be an extension of the gate dielectric layer 412.

Figure 6B:
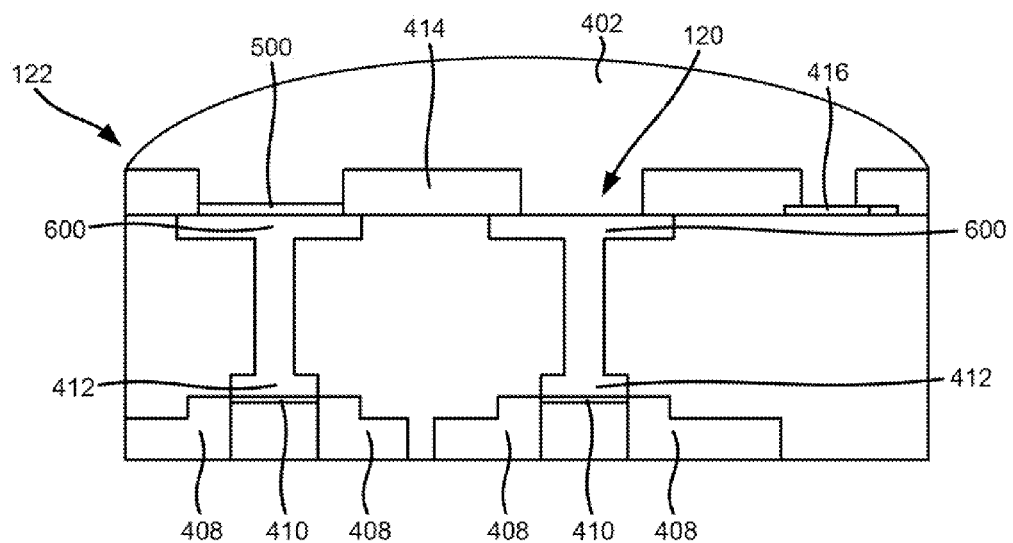
FIG. 6B illustrates a side view of an embodiment of the active sensor and the control sensor each having an extended gate and an on-chip reference electrode.

FIG. 6B illustrates a side view of another embodiment of the active sensor 120 and the control sensor 122 each having the extended gate 600 and an on-chip reference electrode 416 adjacent to the active sensor 120. As shown in FIGS. 6A and 6B, only the extended gate is exposed to the liquid. The extended gate can interact with particles in the solution. The extended gate can reduce the amount of material needed to make the active sensor 120.

Figure 7:
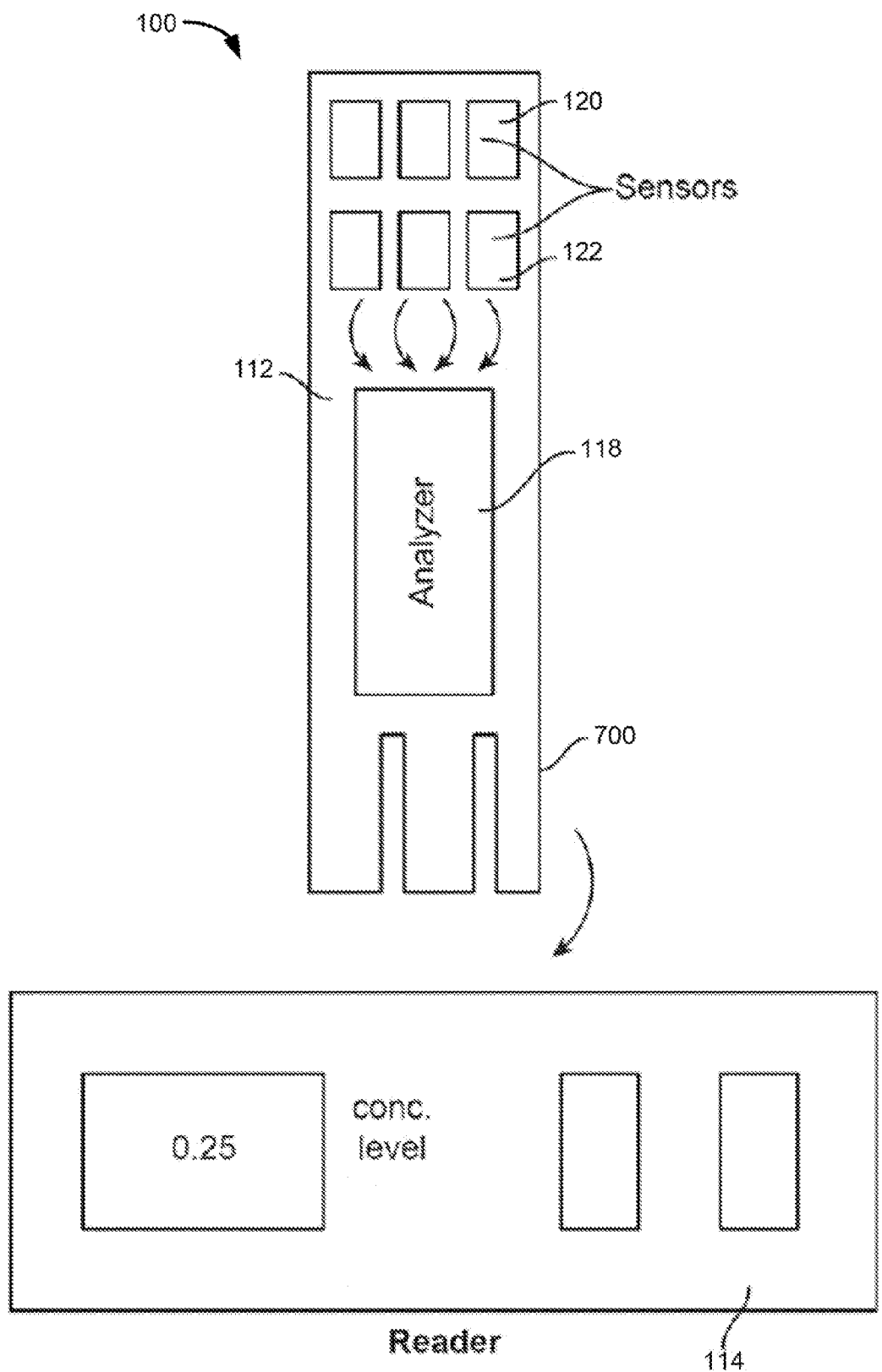
FIG. 7 illustrates an embodiment of the system on a disposable strip.

FIG. 7 illustrates an embodiment of the system 100 fabricated or designed as a disposable strip 700. The disposable strip 700 can comprise a number of active sensors 120 and control sensors 122 and an analyzer 118 disposed on a strip substrate. In one embodiment, sample effluent 134 resulting from step 1E or step 1D depicted in FIG. 1 can be introduced to one end of the disposable strip 700 and the other end of the disposable strip 700 can be electrically coupled to or fed into the reader 114. In another embodiment, a fluid sample 124 can be introduced to one end of the disposable strip 700 as shown in step 2A of FIG. 2 and sample effluent 134 can flow to the active sensors 120, the control sensors 122, or a combination thereof on the disposable strip 700. Although not shown in FIG. 7, substrate wells 200 such as the active wells 206 and the control wells 208 of FIG. 2 can be disposed on the strip substrate upstream from the sensors 116. The reader 114 can then assess the susceptibility of an infectious agent 102 in the fluid sample 124 to the anti-infective 104 introduced to or coated on the disposable strip 700.

Figure 8:
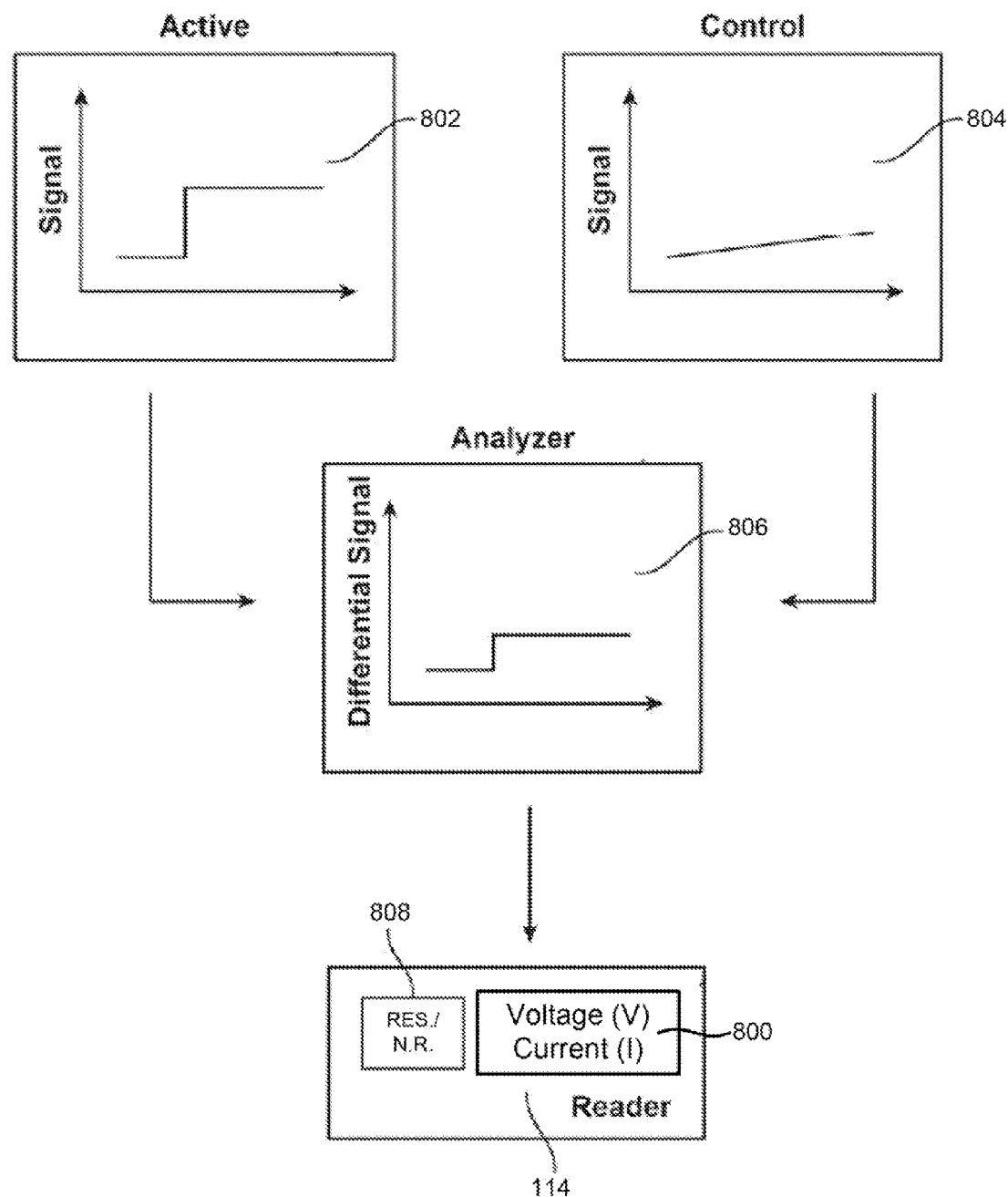
FIG. 8 illustrates the analyzer and the reader processing signals outputted by the active sensor and the control sensor.

FIG. 8 illustrates one embodiment of the analyzer 118 and the reader 114 processing signals outputted by the active sensor 120 and the control sensor 122. The analyzer 118, the reader 114, or a combination thereof can monitor the electrical characteristic 800 of the sensors 116 including the active sensor 120, the control sensor 122, or a combination thereof.

The active sensor 120 can produce an active signal 802. The active signal 802 can be indicative of a change in the electrical characteristic 800 of the active sensor 120. For example, the active signal 802 can be indicative of a change in the current, the voltage, the threshold voltage, the capacitance, or the resistance of the active sensor 120. The active sensor 120 can exhibit a change in its electrical characteristic 800 due to a change in the solution characteristic 136 of a measured liquid 402 contacting or introduced to the active sensor 120. For example, the active sensor 120 can exhibit a change in its electrical characteristic 800 due to a change in the solution characteristic 136 of the sample effluent 134 introduced to the active sensor 120. As a more specific example, the change in the solution characteristic 136 can be change in the concentration of an ion or a change in the pH of the measured liquid 402 contacting or introduced to the active sensor 120.

The control sensor 122 can produce a control signal 804. The control signal can be indicative of a change in the electrical characteristic 800 of the control sensor 122. The control signal can be analyzed relative to the reference electrode. For example, the control signal 804 can be indicative of the change in the current, the voltage, the threshold voltage, the capacitance, or the resistance of the control sensor 122. Similar to the active sensor 120, the control sensor 122 can exhibit a change in its electrical characteristic 800 due to a change in the solution characteristic 136 of a measured liquid 402 contacting or introduced to the control sensor 122.

The analyzer 118 can receive as inputs the active signal 802 from the active sensor 120 and the control signal 804 from the control sensor 122. The analyzer 118 can produce a differential signal 806. In one embodiment, the differential signal 806 can be a difference between the active signal 802 and the control signal 804. The differential signal 806 or ΔS can also be indicative of a change in the electrical characteristic 800 of the active sensor 120 or the control sensor 122 or a difference between the electrical characteristic 800 of the active sensor 120 and the control sensor 122. The reader 114 and the analyzer 118 can also provide a feedback loop to control the active sensor 120.

The analyzer 118 can also convert the active signal 802 and the control signal 804 from analog to digital. The differential signal 806 can be transmitted to the reader 114, and used to assess the susceptibility of the infectious agent 102 in the fluid sample 124 to one or more anti-infectives 104. The reader 114 can also provide an output signal 808 assessing the susceptibility of the infectious agent 102 to one or more anti-infectives 104. In one embodiment, the reader 114 can provide an output signal 808 indicating whether the infectious agent 102 is resistant or sensitive to an anti-infective 104. In another embodiment, the reader 114 can provide an output signal 808 indicating a level of susceptibility of the infectious agent 102 to one or more anti-infectives 104 such as susceptible, mildly susceptible, or resistant.

Figure 9:
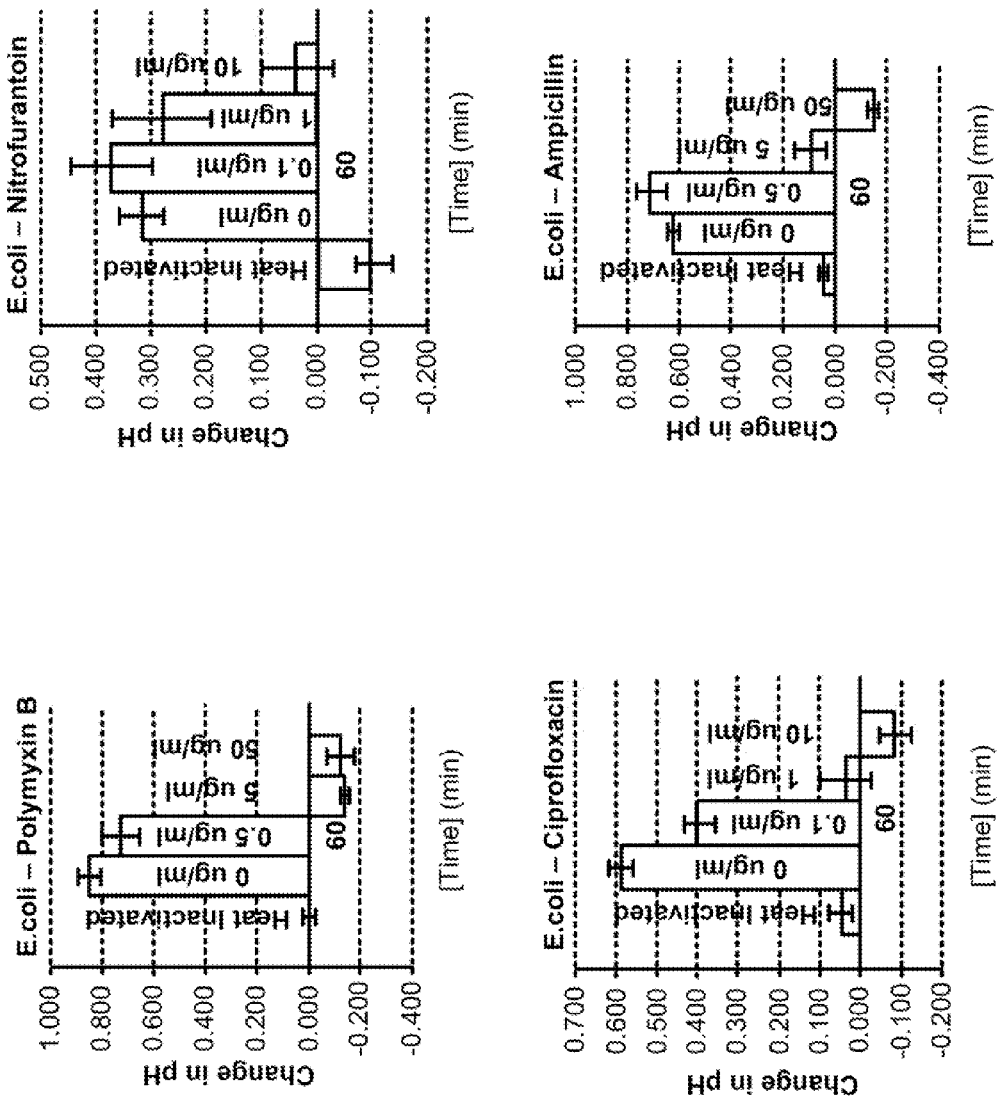
FIG. 9 illustrates experimental results of experiments conducted using the methods and systems described herein.

FIG. 9 illustrates experimental results of experiments conducted using the methods and system 100 described herein. The graphs in FIG. 9 show a change in the solution characteristic 136 of the measured liquid 402, such as the sample effluent 134, monitored by the system 100 at a specific point in time. In this case, the graphs in FIG. 9 show the change in the solution characteristic 136 of the measured liquid 402 sixty (60) minutes after an anti-infective 104 is introduced to the filter 110, the substrate wells 200, or a combination thereof comprising the infectious agent 102.

As shown in FIG. 9, the change in the solution characteristic 136 can be a change in the pH of the measured liquid 402. For example, the graphs in FIG. 9 show the effects of various anti-infectives 104 on *E. coli*. In this example, *E. coli* can be one of the infectious agents 102 present in the fluid sample 124 applied or introduced to the system 100. As shown in FIG. 9, a change in the solution characteristic 136, such as a change in the pH, can indicate resistance of the infectious agent 102 to the anti-infective 104 while a lack of a change or an insignificant change in the solution characteristic 136 can indicate a susceptibility of the infectious agent 102 to the anti-infective 104. An insignificant change in the solution characteristic 136 can be a change below a statistically significant percentage or threshold value.

For example, one of the graphs shows the effects of the anti-infective 104 nitrofurantoin on the pH of the measured liquid 402, such as the sample effluent 134, 60 minutes after *E. coli* from the fluid sample 124 is exposed to nitrofurantoin of various concentrations. As can be seen in the graph, the *E. coli* in the fluid sample 124 can be resistant to approximately 1 μg/ml of nitrofurantoin but can be susceptible when exposed to approximately 10 μg/ml of nitrofurantoin.

Also, for example, another one of the graphs shows the effects of the anti-infective ciprofloxacin on the pH of the measured liquid 402, such as the sample effluent 134, 60 minutes after *E. coli* from the fluid sample 124 is exposed to ciprofloxacin of various concentrations. This graph shows that the systems, devices, and methods disclosed herein can be used to determine the minimal inhibitory concentration (MIC) of an anti-infective on an infectious agent. As can be seen in the graph, the *E. coli* in the fluid sample 124 can be resistant to approximately 0.1 μg/ml of ciprofloxacin but can be susceptible when exposed to approximately 1 μg/ml of nitrofurantoin. In this case, 1 μg/ml can be the MIC of nitrofurantoin on the *E. coli* isolated from the fluid sample 124.

Figure 10:
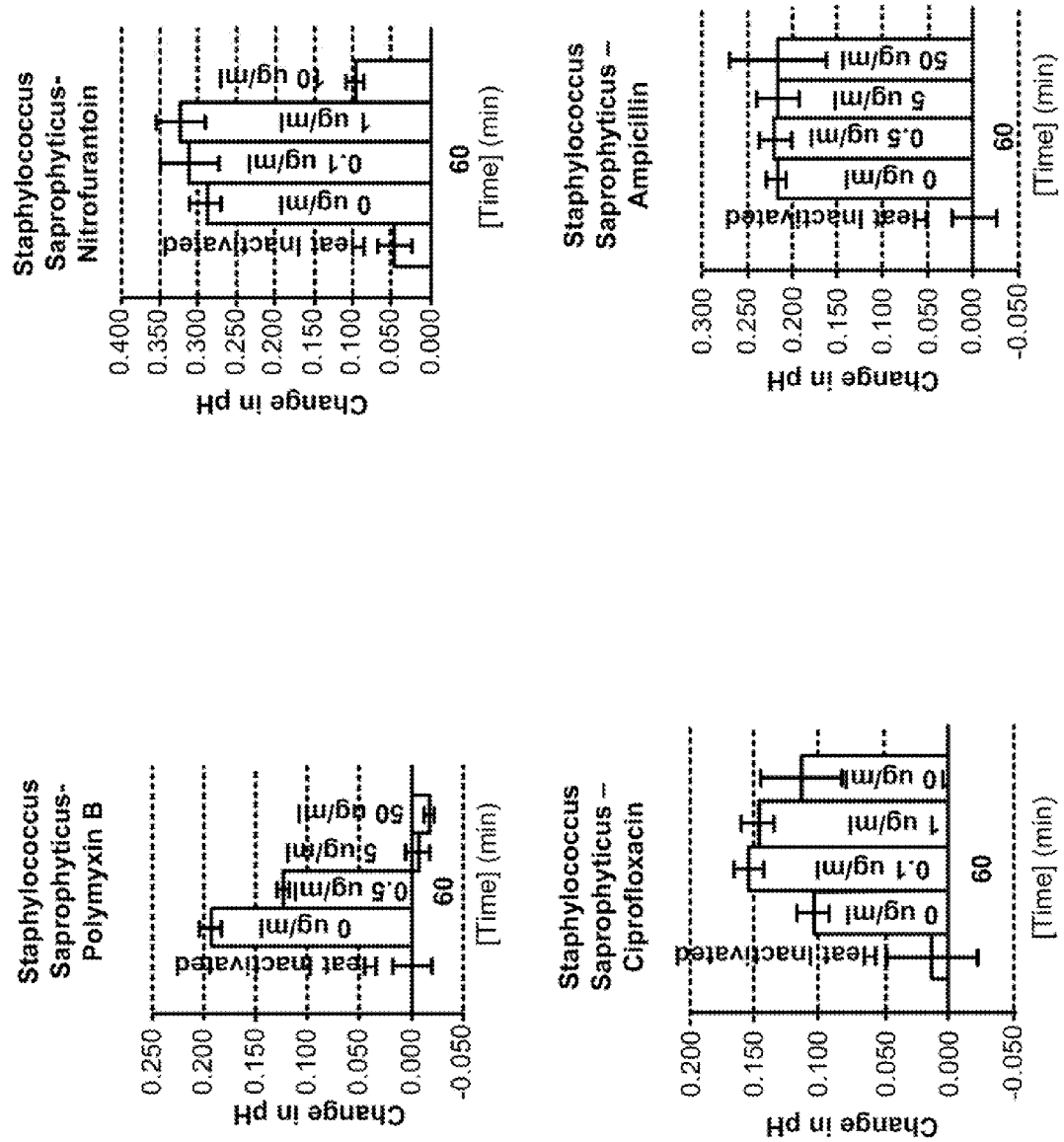
FIG. 10 illustrates additional experimental results of experiments conducted using the methods and systems described herein.

FIG. 10 illustrates additional experimental results of experiments conducted using the methods and system 100 described herein. The graphs in FIG. 10 show the effects of various anti-infectives 104 on the bacteria *Staphylococcus*

*saprophyticus*. In these examples, *Staphylococcus saprophyticus* can be one of the infectious agents 102 present in the fluid sample 124 applied or introduced to the system 100.

For example, one of the graphs shows the effects of the anti-infective 104 ampicillin on the pH of the measured liquid 402, such as the sample effluent 134, 60 minutes after *Staphylococcus saprophyticus* from the fluid sample 124 is exposed to ampicillin of various concentrations. As can be seen in the graph, the *Staphylococcus saprophyticus* in the fluid sample 124 can be resistant to ampicillin when up to 50 µg/ml of ampicillin is introduced to filters or wells comprising the infectious agent 102.

Also, for example, another one of the graphs shows the effects of the anti-infective nitrofurantoin on the pH of the measured liquid 402, such as the sample effluent 134, 60 minutes after *Staphylococcus saprophyticus* from the fluid sample 124 is exposed to nitrofurantoin of various concentrations. As can be seen in the graph, the *Staphylococcus saprophyticus* in the fluid sample 124 can be resistant to approximately 1 µg/ml of nitrofurantoin but can be susceptible when exposed to concentrations higher than 1 µg/ml of nitrofurantoin.

Figure 11:
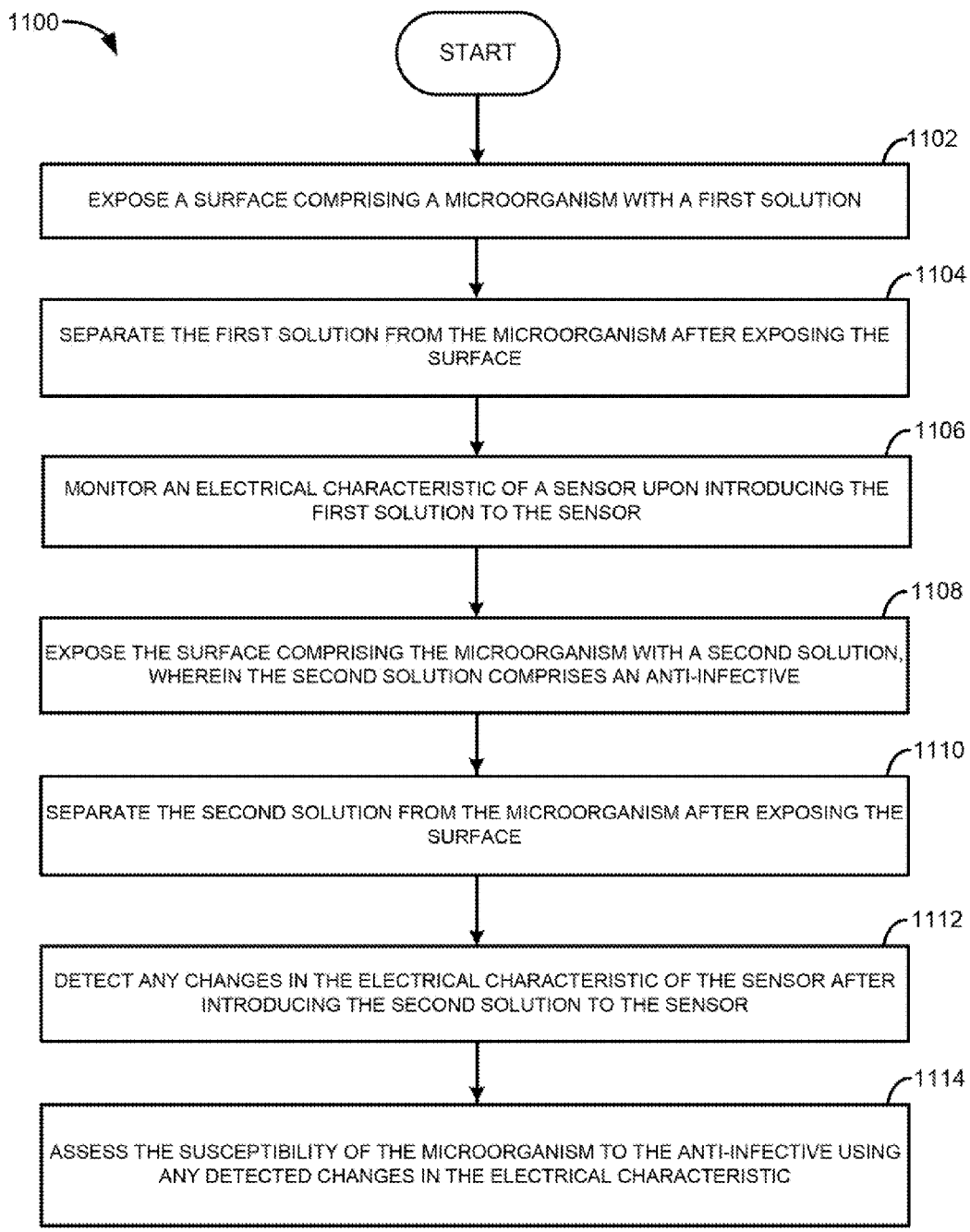
FIG. 11 illustrates an embodiment of a method for detecting a susceptibility of an infectious agent to one or more anti-infectives.

FIG. 11 illustrates an embodiment of a method 1100 for detecting a susceptibility of an infectious agent 102 to one or more anti-infectives 104. The method 1100 can include exposing a surface, such as the filter surface 126 or the substrate surface 202, comprising the infectious agent 102 with a first solution, such as the nutrient solution 130, in a step 1102. The method 1100 can also include separating the first solution from the infectious agent 102 after exposing the surface in a step 1104. The method 1100 can further include monitoring an electrical characteristic 800 of a sensor 116 upon introducing the first solution to the sensor 116 in a step 1106. The method 1100 can also include exposing the surface comprising the infectious agent 102 with a second solution, such as additional nutrient solution 130, wherein the second solution comprises an anti-infective 104 in a step 1108. The method 1100 can further include separating the second solution from the infectious agent 102 after exposing the surface in a step 1110. The method 1100 can also include detecting any changes in the electrical characteristic 800 of the sensor 116 after introducing the second solution to the sensor 116 in a step 1112. The method 1100 can further include assessing the susceptibility of the infectious agent 102 to the anti-infective 104 using any detected changes in the electrical characteristic 800 of the sensor 116 in a step 1114.

Figure 12:
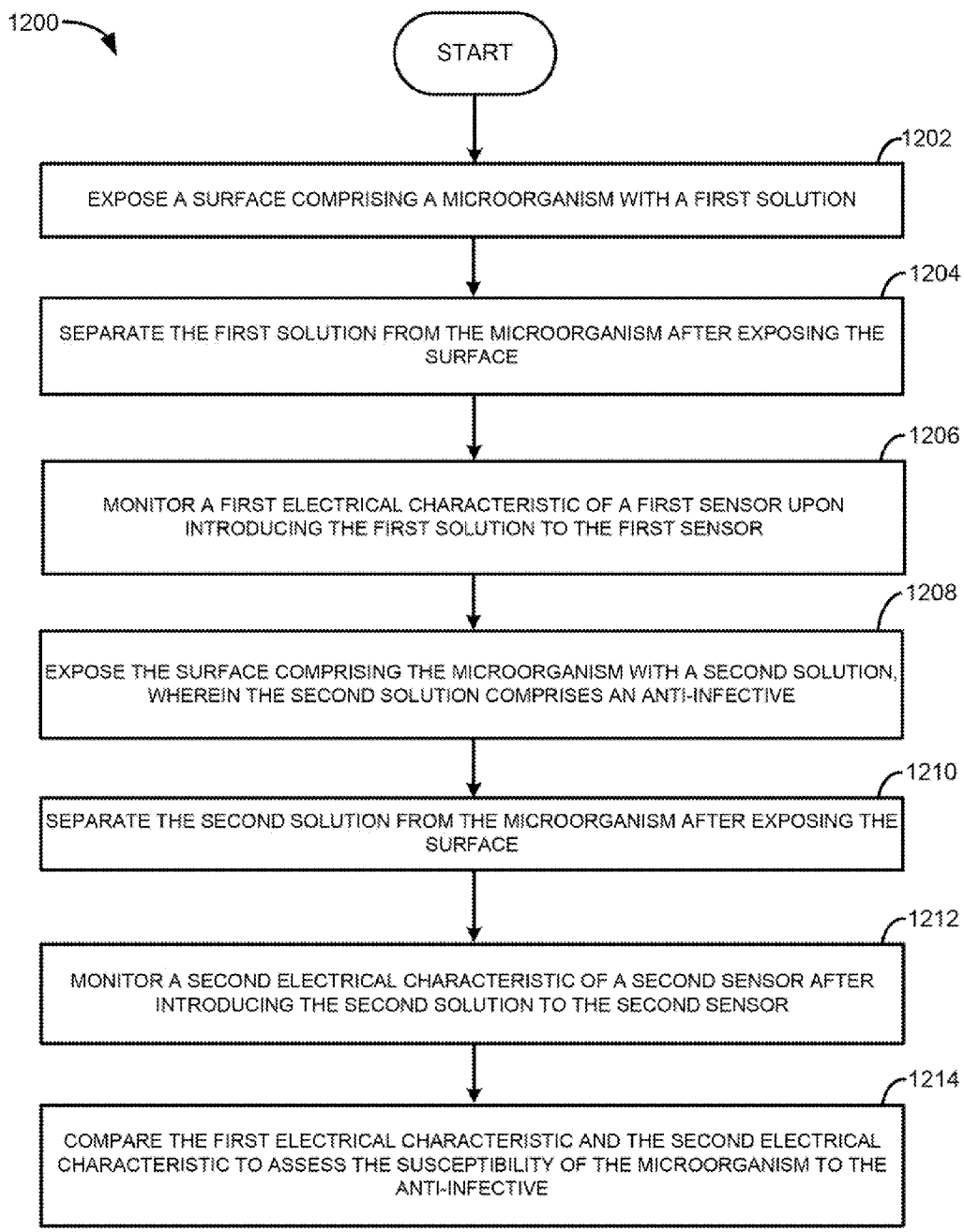
FIG. 12 illustrates another embodiment of the method for detecting a susceptibility of an infectious agent to one or more anti-infectives.

FIG. 12 illustrates another method 1200 for detecting a susceptibility of an infectious agent 102 to one or more anti-infectives 104. The method 1200 can include exposing a surface, such as the filter surface 126 or the substrate surface 202, comprising the infectious agent 102 with a first solution, such as the nutrient solution 130, in a step 1202. The method 1200 can also include separating the first solution from the infectious agent 102 after exposing the surface in a step 1204. The method 1200 can further include monitoring a first electrical characteristic of a first sensor, such as the control sensor 122, upon introducing the first solution to the first sensor in a step 1206. The method 1200 can also include exposing the surface comprising the infectious agent 102 with a second solution, such as additional nutrient solution 130, wherein the second solution comprises an anti-infective 104 in a step 1208. The method 1200 can further include separating the second solution from the infectious agent 102 after exposing the surface in a step 1210. The method 1200 can also include monitoring a second electrical characteristic of a second sensor, such as the active sensor 120, after introducing the second solution to the second sensor in a step 1212. The method 1200 can further include comparing the first electrical characteristic and the second electrical characteristic to assess the susceptibility of the infectious agent 102 to the anti-infective 104 in a step 1214.

Figure 13:
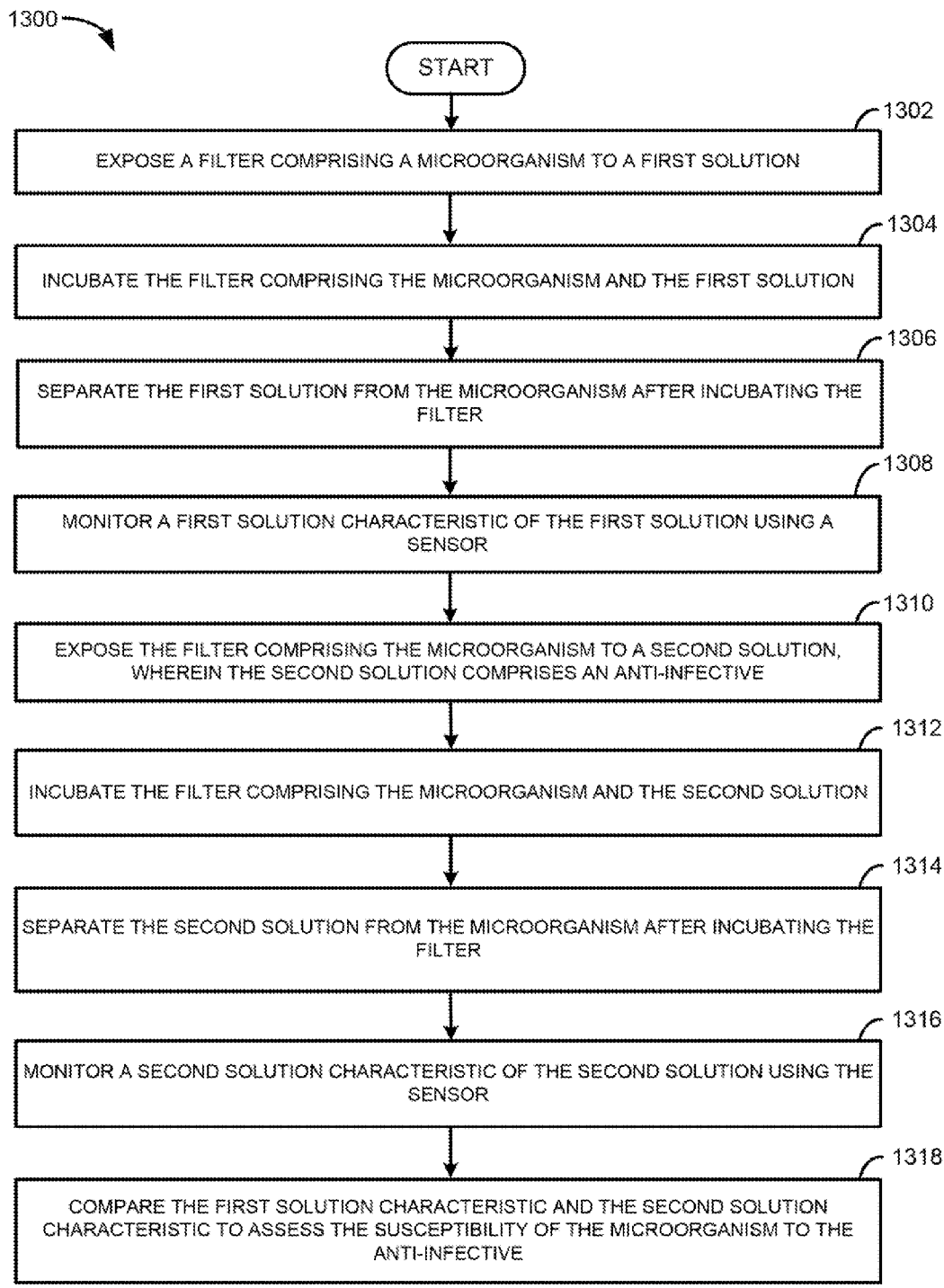
FIG. 13 illustrates yet another embodiment of the method for detecting a susceptibility of an infectious agent to one or more anti-infectives.

FIG. 13 illustrates another method 1300 for detecting a susceptibility of an infectious agent 102 to one or more anti-infectives 104. The method 1300 can include exposing a filter 110 comprising an infectious agent 102 to a first solution, such as the nutrient solution 130 in a step 1302. The method 1300 can also include incubating the filter 110 comprising the infectious agent 102 and the first solution in a step 1304. The method 1300 can also include separating the first solution from the infectious agent 102 after incubating the filter 110 in a step 1306. The method 1300 can also include monitoring a first solution characteristic of the first solution using a sensor or a sensor device 300, such as an ISFET sensor, in a step 1308. The method 1300 can also include exposing the filter 110 comprising the infectious agent 102 to a second solution, wherein the second solution comprises an anti-infective 104 in a step 1310. The method 1300 can also include incubating the filter 110 comprising the infectious agent 102 and the second solution in a step 1312. The method 1300 can also include separating the second solution from the infectious agent 102 after incubating the filter 110 in a step 1314. The method 1300 can also include monitoring a second solution characteristic of the second solution using the sensor 116 in a step 1316. The method 1300 can also include comparing the first solution characteristic and the second solution characteristic to assess the susceptibility of the infectious agent 102 to the anti-infective 104 in a step 1318.

Figure 14:
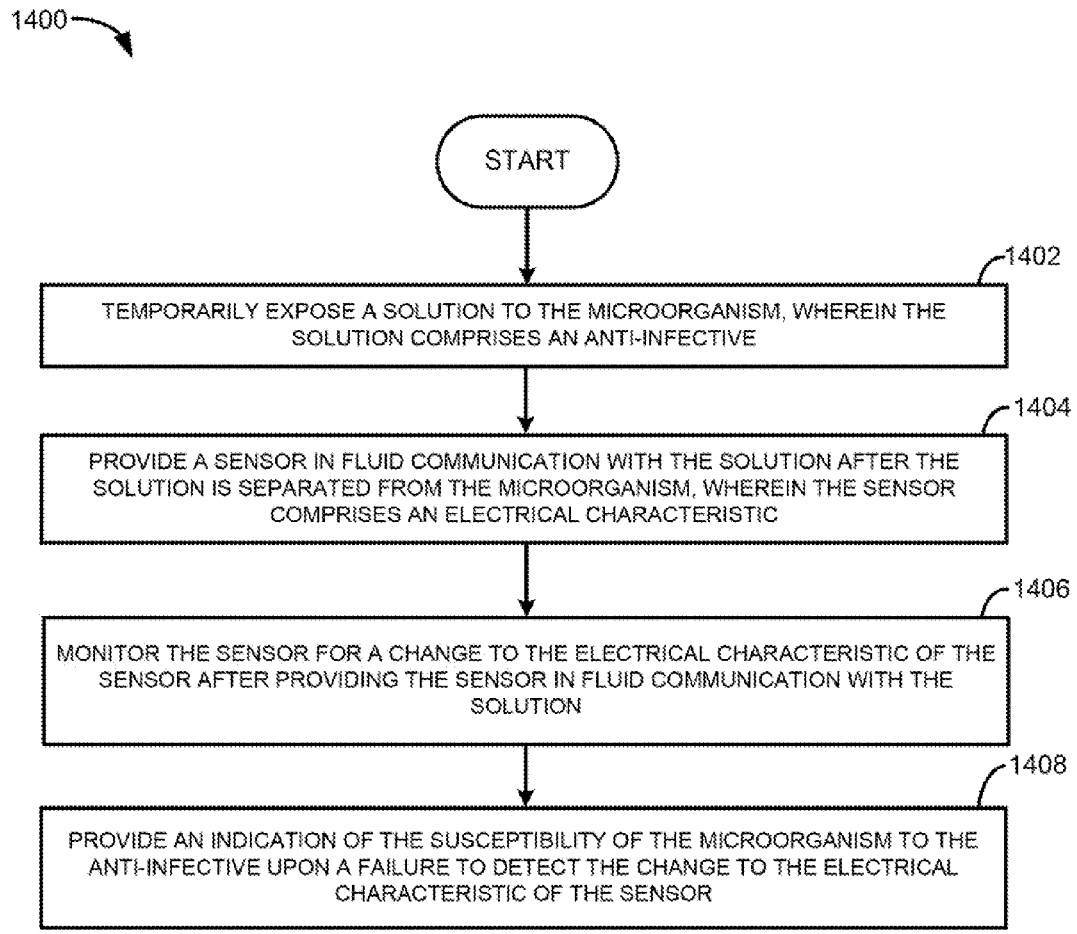
FIG. 14 illustrates another embodiment of the method for detecting a susceptibility of an infectious agent to one or more anti-infectives.

FIG. 14 illustrates another method 1400 for detecting a susceptibility of an infectious agent 102 to one or more anti-infectives 104. The method 1400 can include temporarily exposing a solution, such as the nutrient solution 130, to the infectious agent 102, wherein the solution comprises an anti-infective 104 in a step 1402. The method 1400 can also include providing a sensor 116 in fluid communication with the solution after the solution is separated from the infectious agent 102, wherein the sensor 116 comprises an electrical characteristic 800 in a step 1404. The method 1400 can also include monitoring the sensor 116 for a change to the electrical characteristic 800 of the sensor 116 after providing the sensor 116 in fluid communication with the solution in a step 1406. The method 1400 can also include providing an indication of the susceptibility of the infectious agent 102 to the anti-infective 104 upon a failure to detect the change to the electrical characteristic 800 of the sensor 116 in a step 1408.

Figure 15:
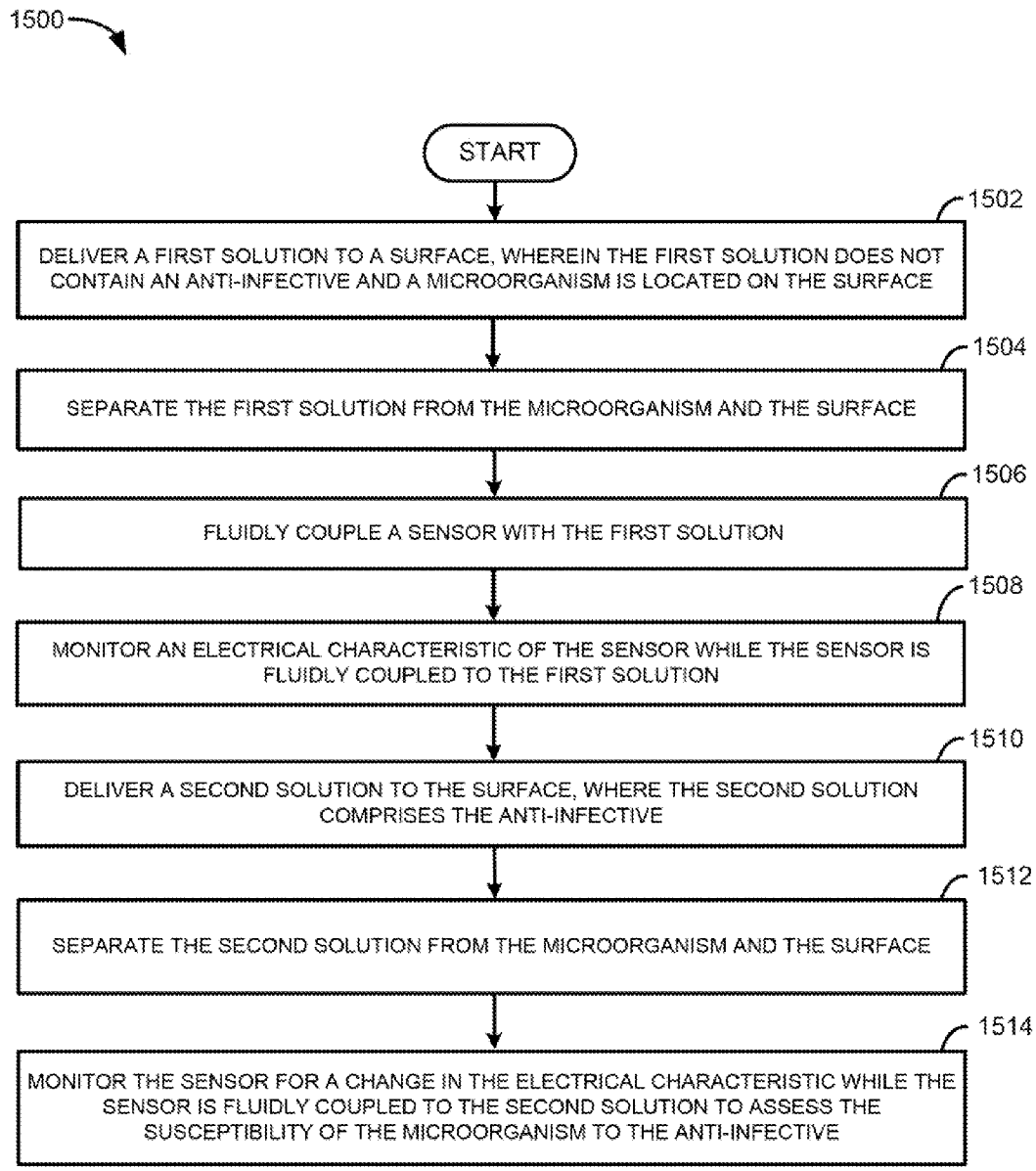
FIG. 15 illustrates a further embodiment of the method for detecting a susceptibility of an infectious agent to one or more anti-infectives.

FIG. 15 illustrates another method 1500 for detecting a susceptibility of an infectious agent 102 to one or more anti-infectives 104. The method 1500 can include delivering a first solution to a surface, such as the filter surface 126 or the substrate surface 202, wherein the first solution does not contain an anti-infective 104 and wherein an infectious agent 102 is located on the surface in a step 1502. The method 1500 can also include separating the first solution from the infectious agent 102 and the surface in a step 1504. The method 1500 can further include fluidly coupling a sensor 116 with the first solution in a step 1506. The method 1500 can also include monitoring an electrical characteristic 800 of the sensor 116 while the sensor 116 is fluidly coupled to the first solution in a step 1508. The method 1500 can further include delivering a second solution to the surface, where the second solution comprises the anti-infective 104 in a step 1510. The method 1500 can also include separating the second solution from the infectious agent 102 and the surface in a step 1512. The method 1500 can further include monitoring the sensor 116 for a change in the electrical characteristic 800 while the sensor 116 is fluidly coupled to the second solution to assess the susceptibility of the infectious agent 102 to the anti-infective 104 in a step 1514.

Figure 16:
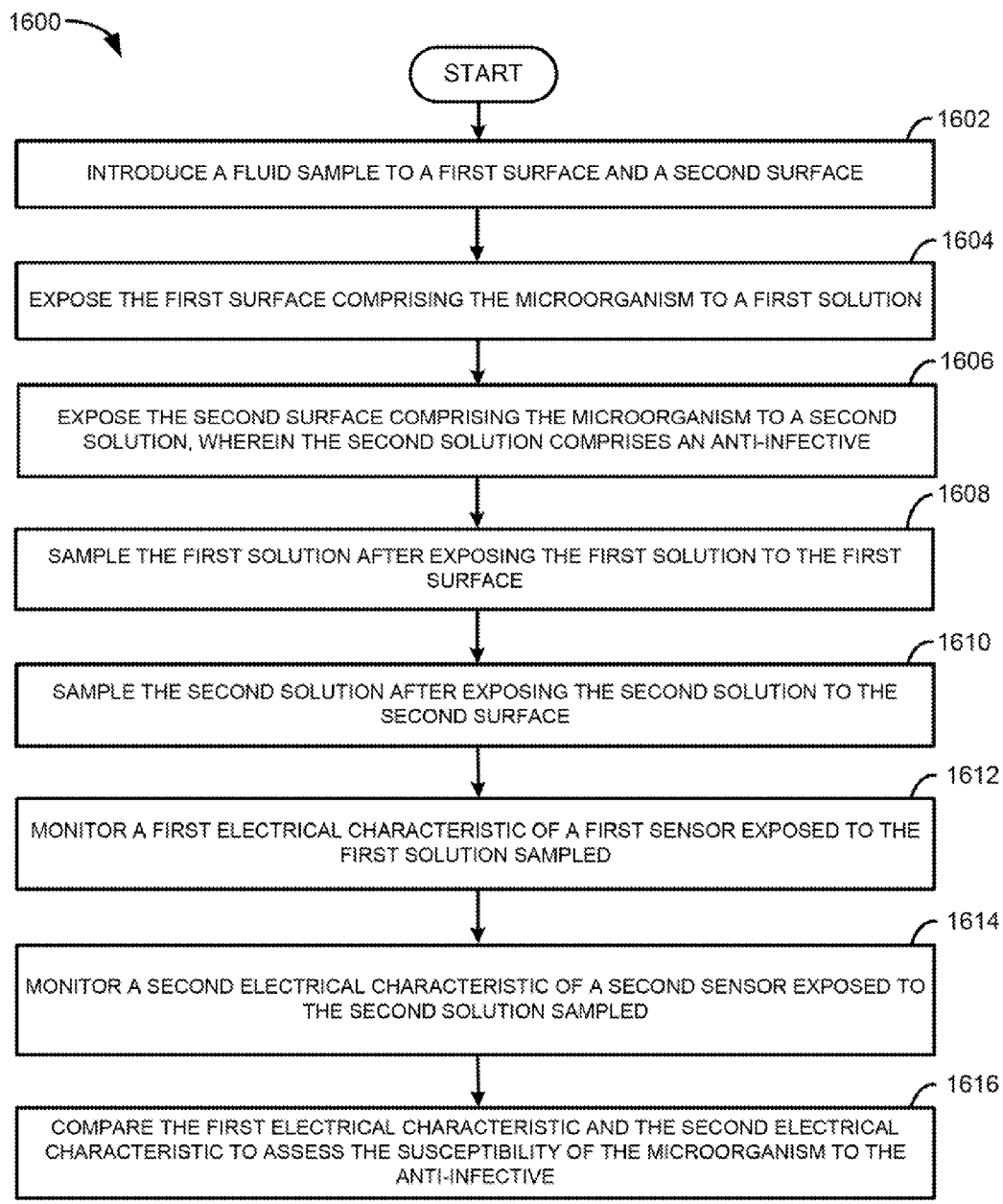
FIG. 16 illustrates another embodiment of the method for detecting a susceptibility of an infectious agent to one or more anti-infectives.

FIG. 16 illustrates another method 1600 for detecting a susceptibility of an infectious agent 102 to one or more anti-infectives 104. The method 1600 can include introducing a fluid sample 124 to a first surface, such as the first filter surface 126A, and a second surface, such as the second filter surface 126B, in a step 1602. The method 1600 can also include exposing the first surface to a first solution, such as the nutrient solution 130, in a step 1604. The first surface can comprise the infectious agent 102 when the infectious agent 102 is present in the fluid sample 124.

The method 1600 can also include exposing the second surface to a second solution, such as additional instances of the nutrient solution 130 in a step 1606. The second surface can comprise one or more anti-infectives 104 or anti-infectives of differing concentrations. The second surface can also comprise the infectious agent 102 when the infectious agent 102 is present in the fluid sample 124.

The method 1600 can also include sampling the first solution after exposing the first solution to the first surface in step 1608. Sampling the first solution can include sampling the effluent or outflow of the first solution, such as the first sample effluent 134A. In one embodiment, sampling the first solution can also involve separating the first solution from the first surface so the first solution is not in fluid communication with the first surface, the infectious agent 102 on the first surface, or a combination thereof when sampled. The method 1600 can also include sampling the second solution after exposing the second solution to the second surface in step 1610. Sampling the second solution can include sampling the effluent or outflow of the second solution, such as the second sample effluent 134B. In one embodiment, sampling the second solution can also involve separating the second solution from the second surface so the second solution is not in fluid communication with the second surface, the infectious agent 102 on the second surface, or a combination thereof when sampled.

The method 1600 can also include monitoring a first electrical characteristic of a first sensor 116A exposed to the first solution sampled in step 1612. The method 1600 can also include monitoring a second electrical characteristic of a second sensor 116B exposed to the second solution sampled in step 1614. The method 1600 can further include comparing the first electrical characteristic and the second electrical characteristic to assess the susceptibility of the infectious agent 102 to the anti-infective 104 in step 1616.

Figure 17:
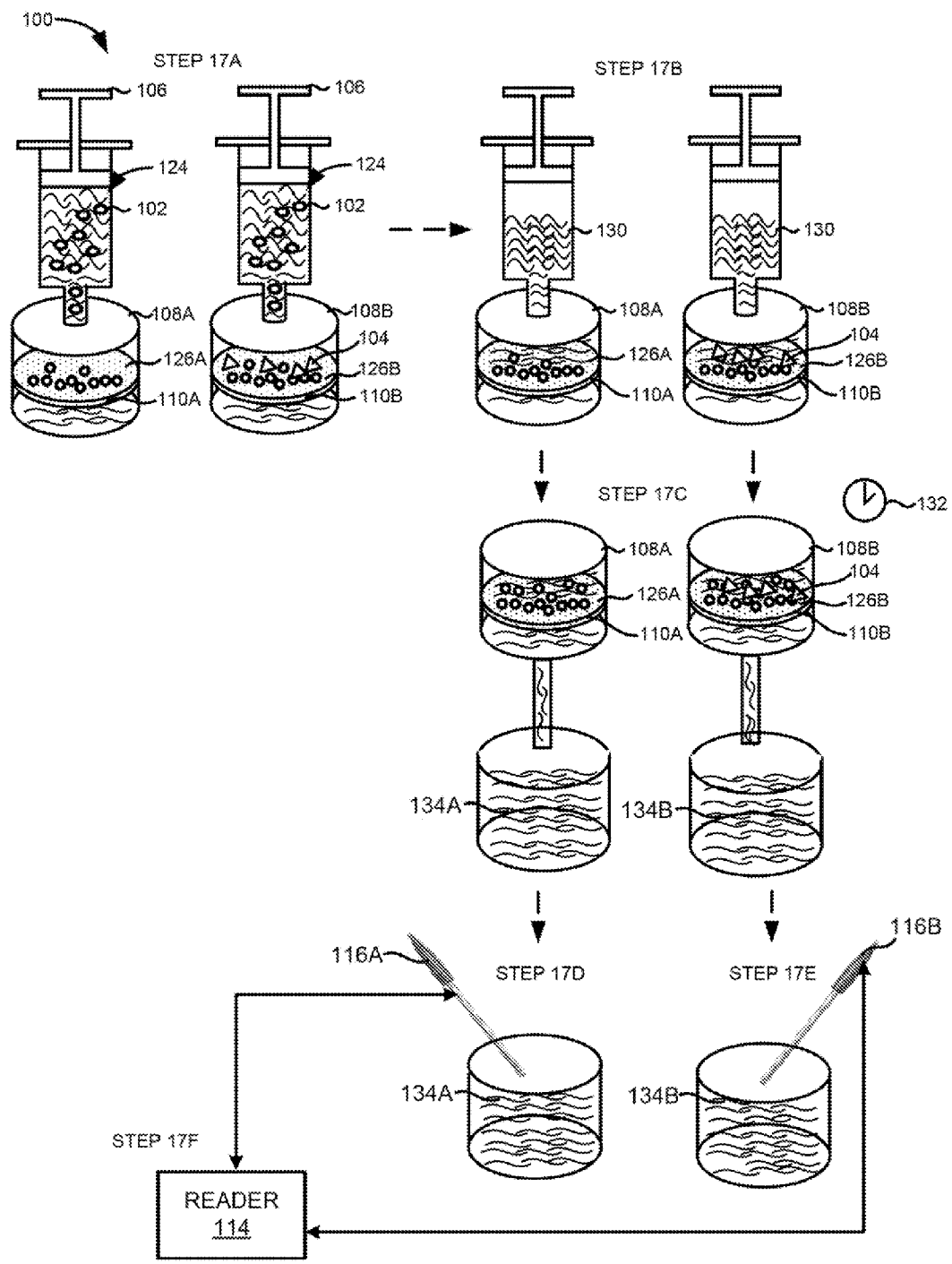
FIG. 17 illustrates another embodiment of a system for detecting a susceptibility of an infectious agent to one or more anti-infectives.

FIG. 17 illustrates another embodiment of the system 100 for detecting or assessing the susceptibility of an infectious agent 102 to an anti-infective 104. The infectious agent 102 can be a bacteria, a fungus, a virus, or a prion.

The system 100 can comprise the fluid delivery device 106, a first filter housing 108A containing a first filter 110A, a second filter housing 108B containing a second filter 110B, a first sensor 116A, a second sensor 116B, and the reader 114. The first sensor 116A can be any of the control sensor 122 or the active sensor 120. The second sensor 116B can also be any of the active sensor 120 or the control sensor 122.

In an alternative embodiment contemplated by the present disclosure but not shown in FIG. 17, the system 100 can comprise the fluid delivery device 106, a first filter housing 108A containing a first filter 110A, a second filter housing 108B containing a second filter 110B, a sensor 116, and the reader 114.

In some instances, the fluid sample 124 can contain the infectious agent 102. The system 100 can detect or assess the level of susceptibility of the infectious agent 102 in the fluid sample 124 to an anti-infective 104. The system 100 can also be used to initially determine the presence or absence of an infectious agent 102 in the fluid sample 124.

As illustrated in FIG. 17, the fluid delivery device 106 can deliver or inject the fluid sample 124 into the first filter housing 108A and the second filter housing 108B in step 17A. The fluid delivery device 106 can be a pump. For example, the fluid delivery device 106 can be a hydraulic pump, a pneumatic pump, a syringe pump, or a combination thereof. In other embodiments, the fluid delivery device 106 can be an injection cartridge, a microfluidic channel, a pipette, a reaction tube, a capillary, a test tube, a combination thereof, or a portion therein.

The first filter housing 108A or the second filter housing 108B can be a container or vessel configured to secure or enclose the first filter 110A or the second filter 110B, respectively. For example, the first filter housing 108A or the second filter housing 108B can be a protective chamber. The protective chamber can be an electrically isolated environment. The protective chamber can also be a temperature controlled chamber, a light controlled chamber, or a combination thereof.

The first filter 110A, the second filter 110B, or a combination thereof can be a non-clogging filter. The first filter surface 126A can be a non-clogging filter surface. The second filter surface 126B can also be a non-clogging filter surface. The first filter 110A, the second filter 110B, or a combination thereof can also have filter pores of sequentially smaller pore size. For example, the first filter 110A, the second filter 110B, or a combination thereof can have larger filter pores at the top of the filter and progressively smaller filters pores toward the bottom of the filter. Although not shown in FIG. 17, it is contemplated by this disclosure that the first filter 110A or the second filter 110B can refer to a plurality of filters in a stacked arrangement.

The first filter 110A can comprise the infectious agent 102 when the fluid sample 124 introduced to the first filter 110A comprises or carries the infectious agent 102. The second filter 110B can also comprise the infectious agent 102 when the fluid sample 124 introduced to the second filter 110B comprises or carries the infectious agent 102.

The first filter 110A can be a mesh or matrix structure for isolating or separating the infectious agent 102 or other molecules or cells from the supernatant of the fluid sample 124. The second filter 110B can also be a mesh or matrix structure for isolating or separating the infectious agent 102 or other molecules or cells from the supernatant of the fluid sample 124. In certain embodiments, the first filter 110A or the second filter 110B can be selected from the group consisting of cellulose acetate, regenerated cellulose, nylon, polystyrene, polyvinylidene fluoride (PVDF), polyethersulfone (PES), polytetrafluoroethylene (PTFE), or a combination thereof.

The first filter 110A can comprise a first filter surface 126A. The first filter surface 126A can be the portion of the first filter 110A used to isolate or trap the infectious agent 102. The first filter surface 126A can include an external surface, an internal surface extending into the first filter 110A, or a combination thereof.

The second filter 110B can comprise a second filter surface 126B. The second filter surface 126B can be the portion of the second filter 110B used to isolate or trap the infectious agent 102. The second filter surface 126B can include an external surface, an internal surface extending into the second filter 110B, or a combination thereof.

The second filter 110B or the second filter surface 126B can comprise the anti-infective 104. The anti-infective 104 can be added or introduced to the second filter surface 126B before or after exposing the second filter surface 126B to the fluid sample 124.

In another embodiment, the anti-infective 104 can be incorporated or embedded into or coated onto the second filter 108B or the second filter surface 126B before exposing the second filter 110B or the second filter surface 126B to the fluid sample 124.

In yet another embodiment, the anti-infective 104 can be introduced through a solution exposed to the first filter 110A, the second filter 110B, or a combination thereof. For example, the anti-infective 104 can be introduced through the nutrient solution 130.

The anti-infective 104 can comprise a bacteriostatic anti-infective, a bactericidal anti-infective, an anti-fungal anti-infective, an antiviral anti-infective, a prion inhibitor, or a combination thereof.

In another embodiment, the anti-infective 104 can be a bacterial growth inhibitor or stimulator. The bacterial growth inhibitor or stimulator can selectively inhibit or promote the growth of gram positive or gram negative bacteria. The bacterial growth inhibitor or stimulator can comprise a dye or a chemical compound. In some embodiments, the dye can include, but is not limited to, Methylene blue, Bromothymol blue, Eosin B, Safranin O, Crystal violet, or a combination thereof. The chemical compound can include, but is not limited to, sodium azide, bile acids, high sodium chloride, or a combination thereof. The anti-infective 104 can also comprise a carbon source other than glucose, such as lactose or mannose, to select for certain bacterial species. The bacterial growth inhibitor, the carbon source, or a combination thereof can also be added to the nutrient solution 130

The first filter housing 108A or the second filter housing 108B can have at least one opening which allows fluid or supernatant from the fluid sample 124 to evacuate the first filter housing 108A or the second filter housing 108B. For example, step 17A can include the additional step of discarding the fluid or supernatant from the fluid sample 124 through the opening after isolating the infectious agent 102 on the first filter surface 126A or the second filter surface 126B.

In an alternative embodiment not shown in FIG. 17, a stimulus solution can be added to the fluid sample 124 before introducing the fluid sample 124 to the first filter 110A or the second filter 110B. The stimulus solution can be a nutrient or growth solution. The stimulus solution can have a different composition than nutrient solution 130. The stimulus solution can be a super nutrient solution.

The fluid sample 124 can also be pre-filtered in a step before step 17A. This pre-filtering step can involve filtering the fluid sample 124 using a filter, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject nutrient solution 130 to the first filter housing 108A, the second filter housing 108B, or a combination thereof in step 17B. The fluid delivery device 106 can continuously or periodically expose the first filter surface 126A, the second filter surface 126B, or a combination thereof to the nutrient solution 130.

After exposing the first filter 110A or the second filter 110B to the nutrient solution 130, the first filter 110A or the second filter 110B can be heated to a temperature of between 30° C. and 40° C. and allowed to incubate for an incubation period 132 in step 17C. In one embodiment, the first filter 110A or the second filter 110B can be incubated while in the first filter housing 108A or the second filter housing 108B, respectively. In another embodiment, the first filter 110A or the second filter 110B can be removed from the first filter housing 108A or the second filter housing 108B, respectively, prior to incubation. In some embodiments, the first filter 110A, the second filter 110B, or a combination thereof can be incubated with the nutrient solution 130. The incubation period 132 can range from 15 minutes to over one hour. In other embodiments, the incubation period 132 can be less than 15 minutes. The incubation period 132 can be adjusted based on the type of infectious agent 102, such as the type of bacteria, fungus, virus, or prion.

The incubation period 132 can also be adjusted based on the amount of the infectious agent 102 present in the fluid sample 124. For example, the incubation period 132 can be increased when the amount of the infectious agent 102 is below a threshold amount. The first filter 110A or the second filter 110B can be allowed to incubate with the nutrient solution 130 in order to promote the proliferation of the infectious agent 102 on the first filter surface 126A or the second filter surface 126B, respectively. One advantage of incubating the first filter 110A and the second filter 110B is to increase the sensitivity of the system 100 to small amounts of the infectious agent 102. For example, incubating the first filter 110A and the second filter 110B can allow the system 100 to reduce its level of detection.

After incubating the first filter 110A or the second filter 110B, the effluent or outflow of the nutrient solution 130 exposed to the first filter 110A or the second filter 110B can be sampled. The effluent or outflow of the nutrient solution 130 exposed to the first filter 110A can be referred to as the first sample effluent 134A. The first sample effluent 134A can be sampled by a first sensor 116A in step 17D. The first sample effluent 134A can be sampled by applying or introducing an aliquot of the first sample effluent 134A to the first sensor 116A. In another embodiment, the first sample effluent 134A can be sampled by inserting a portion of the first sensor 116A directly into the first sample effluent 134A.

The effluent or outflow of the nutrient solution 130 exposed to the second filter 110B can be referred to as the second sample effluent 134B. The second sample effluent 134B can be sampled by a second sensor 116B in step 17E. The second sample effluent 134B can be sampled by applying or introducing an aliquot of the second sample effluent 134B to the second sensor 116B. In another embodiment, the second sample effluent 134B can be sampled by inserting a portion of the second sensor 116B directly into the second sample effluent 134B.

The first sample effluent 134A and the second sample effluent 134B can each comprise a solution characteristic 136. The solution characteristic 136 can refer to one or more attributes of the solution making up the first sample effluent 134A, the second sample effluent 134B, or a combination thereof. For example, the solution characteristic 136 can include a concentration of a solute, an absolute number or molecular count of solutes in solution, a solution temperature, or a combination thereof. For example, the solution characteristic 136 can refer to the amount or concentration of ions, organic molecules such as amino acids, minerals, or other inorganic compounds in the sample effluent 134.

The solution characteristic 136 can vary as a result of natural changes due to the energy use, growth, and metabolism of the infectious agent 102. For example, the solution characteristic 136 can be a direct or indirect byproduct of a cellular activity undertaken by the infectious agent 102 such as cell metabolism or cell growth. The solution characteristic 136 can vary as a result of ions, organic molecules, or minerals produced by or attributed to the infectious agent 102 on the first filter surface 126A, the second filter surface 126B, or a combination thereof.

In one embodiment, the first sample effluent 134A, the second sample effluent 134B, or a combination thereof can comprise hydrogen ions ($H^+$) as a byproduct of bacterial cell metabolism or growth. In other embodiments, the first sample effluent 134A, the second sample effluent 134B, or a combination thereof can comprise adenosine triphosphate (ATP), carbon dioxide ($CO_2$), lactic acid, carbonic acid, nitrates ($NO_3^-$), or a combination thereof produced by or attributed to the infectious agent 102.

In an alternative embodiment contemplated by the present disclosure, the same sensor 116 can be used to sample the first sample effluent 134A and the second sample effluent 134B.

In yet another embodiment, the first sensor 116A, the second sensor 116B, or the one sensor 116, can be integrated into the first filter 110A, the second filter 110B, or a combination thereof. For example, the first sensor 116A can be integrated into the first filter 110A and the second sensor 116B can be integrated into the second filter 110B.

The reader 114 can monitor an electrical characteristic 800 (see FIG. 8) of the first sensor 116A exposed to the first sample effluent 134A in step 17F. The reader 114 can also monitor the electrical characteristic 800 of the second sensor 116B exposed to the second sample effluent 134B in step 17F. In this embodiment, the electrical characteristic 800 of the first sensor 116A can be referred to as a first electrical characteristic and the electrical characteristic 800 of the second sensor 116B can be referred to as the second electrical characteristic.

When only one sensor 116 is used to sample the sample effluents, the reader 114 can monitor the electrical characteristic 800 of the one sensor 116 exposed to the first sample effluent 134A and the reader 114 can also monitor the electrical characteristic 800 of the one sensor 116 exposed to the second sample effluent 134B. In this embodiment, the electrical characteristic 800 of the sensor 116 while sampling the first sample effluent 134A can be referred to as the first electrical characteristic and the electrical characteristic 800 of the sensor 116 while sampling the second sample effluent 134B can be referred to as the second electrical characteristic.

The electrical characteristic 800 can include a current, a voltage, a threshold voltage, a capacitance, a resistance, a noise level, a subthreshold swing, a level of induction, or a combination thereof measured at or near the sensor 116. The reader 114 can be electrically or communicatively coupled to the first sensor 116A, the second sensor 116B, or a combination thereof to monitor the electrical characteristic 800 of the first sensor 116A, the second sensor 116B, or a combination thereof over time. The reader 114 can also be configured to provide a read-out of the electrical characteristic 800 of the first sensor 116A, the second sensor 116B, or a combination thereof. When only one sensor 116 is used to sample the sample effluents, the reader 114 can be electrically or communicatively coupled to the one sensor 116.

In certain embodiments, the reader 114 can be a mobile device, a handheld device, a tablet device, or a computing device such as a laptop or desktop computer. The reader 114 can compare the first electrical characteristic with the second electrical characteristic to assess the susceptibility of the infectious agent 102 to the anti-infective 104.

The first electrical characteristic can differ from the second electrical characteristic when the solution characteristic 136 of the first sample effluent 134A differs from the solution characteristic 136 of the second sample effluent 134B as a result of differences in the solution temperature, the concentration of solutes present in the sample effluents, or the amount of solutes present in the sample effluents. For example, the first electrical characteristic and the second electrical characteristic can differ when the solution characteristic 136 of the first sample effluent 134A and the solution characteristic of the second sample effluent 134B differ in their pH, temperature, the concentration of another ion, or a combination thereof.

The reader 114 can assess the susceptibility of the infectious agent 102 to the anti-infective 104 as a binary assessment or a gradated or tiered assessment. In one embodiment, the reader 114 can assess the susceptibility of the infectious agent 102 as either resistant or non-resistant to the anti-infective 104. In this embodiment, the second filter 110B or the second filter surface 126B can comprise a set amount of the anti-infective 104. The reader 114 can then assess the susceptibility of the infectious agent 102 as either resistant or non-resistant based on any detected differences in first electrical characteristic and the second electrical characteristic.

The reader 114 can assess the susceptibility of the infectious agent 102 as not resistant to the anti-infective 104 when the reader 114 fails to detect a difference or a statistically significant difference between the first electrical characteristic and the second electrical characteristic. More specifically, a statistically significant difference in the electrical characteristic can be a difference exceeding a threshold value.

In other embodiments, the reader 114 can assess the level of susceptibility of the infectious agent 102 on a gradated or tiered scale. For example, the reader 114 can assess the susceptibility of the infectious agent 102 as being resistant, mildly susceptible, or susceptible to the anti-infective 104. In these embodiments, additional filter surfaces, including the second filter surface 126B and a third filter surface, can be used which comprise anti-infectives 104 of different concentrations. While three categories of susceptibility are discussed, it should be understood by one of ordinary skill in the art that four or greater categories of susceptibility or four or greater filters can be used to assess the level of susceptibility of the infectious agent 102 to differing concentrations of the anti-infective 104.

Figure 18:
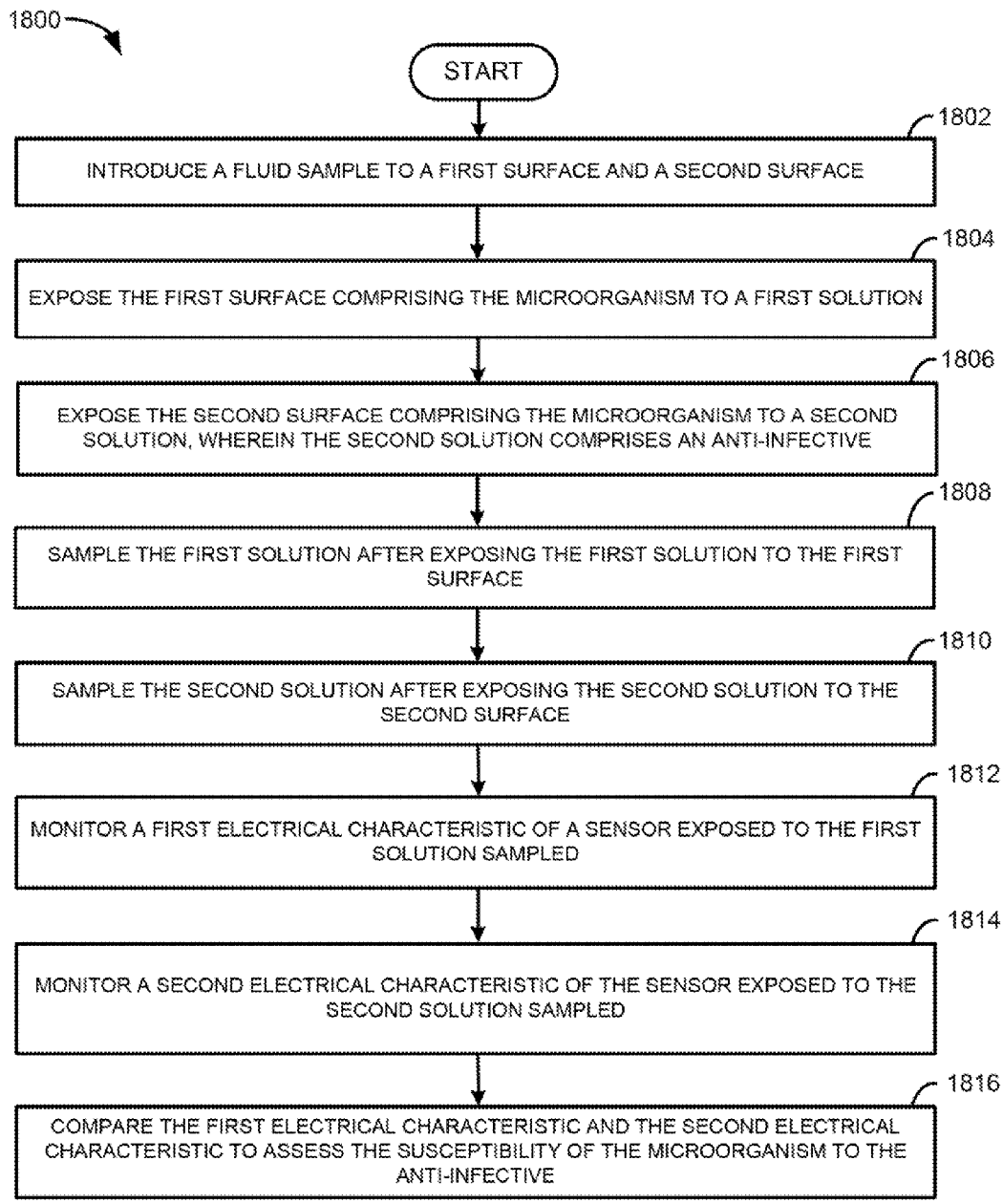
FIG. 18 illustrates another embodiment of a method for detecting a susceptibility of an infectious agent to one or more anti-infectives.

FIG. 18 illustrates another method 1600 for detecting a susceptibility of an infectious agent 102 to one or more anti-infectives 104. The method 1600 can include introducing a fluid sample 124 to a first surface, such as the first filter surface 126A, and a second surface, such as the second filter surface 126B, in a step 1802. The method 1800 can also include exposing the first surface to a first solution, such as the nutrient solution 130, in a step 1804. The first surface can comprise the infectious agent 102 when the infectious agent 102 is present in the fluid sample 124.

The method 1800 can also include exposing the second surface to a second solution, such as additional instances of the nutrient solution 130 in a step 1806. The second surface can comprise one or more anti-infectives 104 or anti-infectives of differing concentrations. The second surface can also comprise the infectious agent 102 when the infectious agent 102 is present in the fluid sample 124.

The method 1800 can also include sampling the first solution after exposing the first solution to the first surface in step 1808. Sampling the first solution can include sampling the effluent or outflow of the first solution, such as the first sample effluent 134A. In one embodiment, sampling the first solution can also involve separating the first solution from the first surface so the first solution is not in fluid communication with the first surface, the infectious agent 102 on the first surface, or a combination thereof. The method 1800 can also include sampling the second solution after exposing the second solution to the second surface in step 1810. Sampling the second solution can include sampling the effluent or outflow of the second solution, such as the second sample effluent 134B. In one embodiment, sampling the second solution can also involve separating the second solution from the second surface so the second solution is not in fluid communication with the second surface, the infectious agent 102 on the second surface, or a combination thereof.

The method 1800 can also include monitoring a first electrical characteristic of a sensor 116 exposed to the first solution sampled in step 1812. The method 1800 can also include monitoring a second electrical characteristic of the sensor 116 exposed to the second solution sampled in step 1814. The method 1800 can further include comparing the first electrical characteristic and the second electrical characteristic to assess the susceptibility of the infectious agent 102 to the anti-infective 104 in step 1816.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method for detecting a susceptibility of a microorganism to an antibiotic, the method comprising:
   exposing a surface comprising the microorganism to a first solution;
   separating the first solution from the microorganism after the first solution is exposed to the surface;
   monitoring an electrical characteristic of a sensor upon introducing the first solution to the sensor, wherein the sensor comprises an on-chip reference electrode and wherein the sensor comprises at least one ion-sensitive field effect transistor (ISFET);
   exposing the surface comprising the microorganism to a second solution, wherein the second solution comprises an antibiotic;
   separating the second solution from the microorganism after the second solution is exposed to the surface;
   detecting any changes in the electrical characteristic of the sensor after introducing the second solution to the sensor; and
   assessing the susceptibility of the microorganism to the antibiotic using any detected changes in the electrical characteristic, wherein the surface is of a filter, and wherein the filter comprises a glass fiber filter and at least one of a nylon filter membrane and a polyethersulfone (PES) filter membrane.

2. The method of claim 1, wherein the change in the electrical characteristic of the sensor indicates a change in a solution characteristic.

3. The method of claim 2, wherein the change in the solution characteristic is a change in a concentration of an ion.

4. The method of claim 1, wherein the susceptibility of the microorganism to the antibiotic is assessed between 10 minutes to 300 minutes.

5. The method of claim 1, wherein the sensor comprises a gate dielectric layer selected from a group consisting of an aluminum oxide layer, a hafnium oxide layer, a zirconium oxide layer, a hafnium silicate layer, a zirconium silicate layer, or any combination thereof.

6. The method of claim 1, wherein the microorganism comprises bacteria selected from the genera consisting of

*Acinetobacter, Aeromonas, Bacillus, Bacteroides, Citrobacter, Clostridium, Enterobacter, Enterococcus, Escherichia, Klebsiella, Morganella, Pandoraea, Proteus, Providencia, Pseudomonas, Ralstonia, Raoultella, Salmonella, Serratia, Shewanella, Shigella, Staphylococcus, Stenotrophomonas, Streptomyces*, or any combination thereof.

7. The method of claim 1, wherein the antibiotic comprises a bacteriostatic antibiotic selected from the group consisting of β-lactams, Aminoglycosides, Ansamycins, Glycopeptides, Lipopeptides, Quinolones, Streptogramins, Sulfonamides, Tetracyclines, Macrolides, Oxazolidinones, or any combination thereof.

8. A method for detecting a susceptibility of a microorganism to an antibiotic, the method comprising:
   exposing a surface comprising the microorganism to a first solution;
   separating the first solution from the microorganism after the first solution is exposed to the surface;
   monitoring a first electrical characteristic of a first sensor upon introducing the first solution to the first sensor, wherein the first sensor comprises a first on-chip reference electrode and wherein the first sensor comprises at least one first ion-sensitive field effect transistor (ISFET);
   exposing the surface comprising the microorganism to a second solution, wherein the second solution comprises an antibiotic;
   separating the second solution from the microorganism after the second solution is exposed to the surface;
   monitoring a second electrical characteristic of a second sensor after introducing the second solution to the second sensor, wherein the second sensor comprises a second on-chip reference electrode and wherein the second sensor comprises at least one second ISFET; and
   comparing the first electrical characteristic and the second electrical characteristic to assess the susceptibility of the microorganism to the antibiotic, wherein the surface is of a filter, wherein the filter comprises a glass fiber filter and at least one of a nylon filter membrane and a polyethersulfone (PES) filter membrane.

9. The method of claim 8, wherein comparing the first electrical characteristic and the second electrical characteristic includes determining a difference between the first electrical characteristic and the second electrical characteristic and the difference between the first electrical characteristic and the second electrical characteristic is a result of a difference in a solution characteristic of the first solution and the second solution.

10. The method of claim 9, wherein the difference in the solution characteristic of the first solution and the second solution is a difference in a concentration of an ion between the first solution and the second solution.

11. The method of claim 8, wherein the susceptibility of the microorganism to the antibiotic is assessed between 10 minutes to 300 minutes.

12. The method of claim 8, wherein at least one of the first sensor and the second sensor comprises a gate dielectric layer selected from a group consisting of an aluminum oxide layer, a hafnium oxide layer, a zirconium oxide layer, a hafnium silicate layer, a zirconium silicate layer, or any combination thereof.

13. The method of claim 8, wherein the microorganism comprises bacteria selected from the genera consisting of *Acinetobacter, Aeromonas, Bacillus, Bacteroides, Citrobacter, Clostridium, Enterobacter, Enterococcus, Escherichia, Klebsiella, Morganella, Pandoraea, Proteus, Providencia, Pseudomonas, Ralstonia, Raoultella, Salmonella, Serratia, Shewanella, Shigella, Staphylococcus, Stenotrophomonas, Streptomyces*, or any combination thereof.

14. The method of claim 8, wherein the antibiotic comprises a bacteriostatic antibiotic selected from the group consisting of β-lactams, Aminoglycosides, Ansamycins Glycopeptides, Lipopeptides, Quinolones, Streptogramins, Sulfonamides, Tetracyclines, Macrolides, Oxazolidinones, or any combination thereof.

15. A method for detecting a susceptibility of a microorganism to an antibiotic, the method comprising:
   temporarily exposing a solution to the microorganism, wherein the solution comprises an antibiotic;
   providing a sensor in fluid communication with the solution after the solution temporarily exposed to the microorganism is separated from the microorganism, wherein the sensor comprises an electrical characteristic, wherein the sensor comprises an on-chip reference electrode, and wherein the sensor comprises at least one ion-sensitive field effect transistor (ISFET);
   monitoring a change in the electrical characteristic of the sensor after providing the sensor in fluid communication with the solution, wherein providing the sensor in fluid communication with the solution involves providing the sensor in fluid communication with the solution after the solution is separated from the microorganism such that the solution is no longer in fluid communication with the microorganism; and
   providing an indication of the susceptibility of the microorganism to the antibiotic when the electrical characteristic of the sensor is unchanged.

16. The method of claim 15, wherein the change in the electrical characteristic of the sensor indicates a change in a concentration of an ion in the solution.

* * * * *